(12) United States Patent
Rabiner et al.

(10) Patent No.: US 9,179,959 B2
(45) Date of Patent: Nov. 10, 2015

(54) SYSTEMS AND METHODS FOR TREATING CONDITIONS AND DISEASES OF THE SPINE

(75) Inventors: Robert A. Rabiner, Tiverton, RI (US); Gene P. DiPoto, Upton, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 511 days.

(21) Appl. No.: 13/335,110

(22) Filed: Dec. 22, 2011

(65) Prior Publication Data

US 2012/0165941 A1 Jun. 28, 2012

Related U.S. Application Data

(60) Provisional application No. 61/426,044, filed on Dec. 22, 2010.

(51) Int. Cl.
*A61F 2/44* (2006.01)
*A61B 17/88* (2006.01)
(Continued)

(52) U.S. Cl.
CPC .......... *A61B 17/8855* (2013.01); *A61B 17/7097* (2013.01); *A61B 17/8836* (2013.01); *A61F 2/441* (2013.01); *A61B 2019/5206* (2013.01); *A61F 2002/30581* (2013.01);
(Continued)

(58) Field of Classification Search
CPC ........... A61B 17/8855; A61B 17/7097; A61B 17/8836; A61B 17/5206; A61F 2/441; A61F 2002/30581; A61F 2002/30583; A61F 2002/30971; A61F 2002/4495
USPC .......................... 623/17.12; 606/99, 246–249
See application file for complete search history.

(56) References Cited

U.S. PATENT DOCUMENTS 4,280,233 A 7/1981 Raab
4,294,251 A 10/1981 Greenwald et al.
(Continued)

FOREIGN PATENT DOCUMENTS

DE 40 28 466 3/1992
EP 0 709 698 5/1996
(Continued)

OTHER PUBLICATIONS

USPTO Office Action in U.S. Appl. No. 13/772,947 mailed Jun. 19, 2013.
(Continued)

*Primary Examiner* — Christopher Beccia
*Assistant Examiner* — Diana S Jones
(74) *Attorney, Agent, or Firm* — Greenberg Traurig, LLP; David J. Dykeman; Roman Fayerberg

(57) ABSTRACT

Systems and methods for treating conditions and diseases of the spine are disclosed herein. A device includes a balloon catheter comprising at least one inner lumen incorporated within an elongated shaft; a distal end having an inner balloon positioned inside and completely surrounded by an outer balloon; and a proximal end having an adapter for passage of at least one of an inflation fluid or a medical instrument; and an optical fiber comprising an outer diameter sized to pass through the inner lumen of the elongated shaft; a nonlinear light-emitting portion of a given length, wherein a portion of a cladding material from the nonlinear light-emitting portion has been removed so that light energy may be emitted along the length of the nonlinear light-emitting portion; and a linear elongated portion for guiding light towards the nonlinear light-emitting portion.

24 Claims, 23 Drawing Sheets

(51) Int. Cl.
   *A61B 17/70* (2006.01)
   *A61B 19/00* (2006.01)
   *A61F 2/30* (2006.01)

(52) U.S. Cl.
   CPC ............... *A61F 2002/30583* (2013.01); *A61F 2002/30971* (2013.01); *A61F 2002/4495* (2013.01)

(56) References Cited

U.S. PATENT DOCUMENTS

| | | |
|---|---|---|
| 4,313,434 A | 2/1982 | Segal |
| 4,341,691 A | 7/1982 | Anuta |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |
| 4,562,598 A | 1/1986 | Kranz |
| 4,686,973 A | 8/1987 | Frisch |
| 4,697,584 A | 10/1987 | Haynes |
| 4,735,625 A | 4/1988 | Davidson |
| 4,870,953 A | 10/1989 | DonMichael et al. |
| 4,888,024 A | 12/1989 | Powlan |
| 4,892,550 A | 1/1990 | Huebsch |
| 4,904,391 A | 2/1990 | Freeman |
| 4,961,424 A | 10/1990 | Kubota et al. |
| 4,963,151 A | 10/1990 | Ducheyne et al. |
| 4,969,888 A | 11/1990 | Scholten et al. |
| 5,030,093 A | 7/1991 | Mitnick |
| 5,049,157 A | 9/1991 | Mittelmeier et al. |
| 5,085,660 A | 2/1992 | Lin |
| 5,092,899 A | 3/1992 | Forte |
| 5,102,413 A | 4/1992 | Poddar |
| 5,108,404 A | 4/1992 | Scholten et al. |
| 5,112,333 A | 5/1992 | Fixel |
| 5,207,669 A | 5/1993 | Baker et al. |
| 5,295,733 A | 3/1994 | LeBegue |
| 5,295,962 A | 3/1994 | Crocker et al. |
| 5,303,718 A | 4/1994 | Krajicek |
| 5,316,550 A | 5/1994 | Forte |
| 5,336,699 A | 8/1994 | Cooke et al. |
| 5,372,598 A | 12/1994 | Luhr et al. |
| 5,376,123 A | 12/1994 | Klaue et al. |
| 5,391,144 A | 2/1995 | Sakurai et al. |
| 5,415,654 A | 5/1995 | Daikuzono |
| 5,423,850 A | 6/1995 | Berger |
| 5,432,876 A | 7/1995 | Appeldorn et al. |
| 5,443,468 A | 8/1995 | Johnson |
| 5,462,552 A | 10/1995 | Kiester |
| 5,480,400 A | 1/1996 | Berger |
| 5,538,514 A | 7/1996 | Hawkins |
| 5,548,676 A | 8/1996 | Savage, Jr. |
| 5,554,111 A | 9/1996 | Morrey et al. |
| 5,556,429 A | 9/1996 | Felt |
| 5,571,204 A | 11/1996 | Nies |
| 5,658,310 A | 8/1997 | Berger |
| 5,658,963 A | 8/1997 | Qian et al. |
| 5,705,181 A | 1/1998 | Cooper et al. |
| 5,707,374 A | 1/1998 | Schmidt |
| 5,713,901 A | 2/1998 | Tock |
| 5,795,353 A | 8/1998 | Felt |
| 5,824,087 A | 10/1998 | Aspden et al. |
| 5,827,289 A | 10/1998 | Reiley et al. |
| 5,888,220 A | 3/1999 | Felt et al. |
| 5,897,557 A | 4/1999 | Chin et al. |
| 5,908,433 A | 6/1999 | Eager et al. |
| 5,972,015 A | 10/1999 | Scribner et al. |
| 5,980,075 A | 11/1999 | Sheaffer |
| 5,980,253 A | 11/1999 | Oxman et al. |
| 5,987,199 A | 11/1999 | Zarian et al. |
| 5,989,230 A | 11/1999 | Frassica |
| 5,997,570 A | 12/1999 | Ligtenberg et al. |
| 6,008,264 A | 12/1999 | Ostler |
| 6,019,761 A | 2/2000 | Gustilo |
| 6,019,774 A | 2/2000 | Weiss et al. |
| 6,033,411 A | 3/2000 | Preissman |
| 6,039,762 A | 3/2000 | McKay |
| 6,042,380 A | 3/2000 | De Rowe |
| 6,048,346 A | 4/2000 | Reiley et al. |
| 6,053,917 A | 4/2000 | Sherman et al. |
| 6,059,789 A | 5/2000 | Dinger et al. |
| 6,066,154 A | 5/2000 | Reiley et al. |
| 6,077,265 A | 6/2000 | Werding et al. |
| 6,079,868 A | 6/2000 | Rydell |
| 6,103,203 A | 8/2000 | Fischer |
| 6,110,176 A | 8/2000 | Shapira |
| 6,121,341 A | 9/2000 | Sawhney et al. |
| 6,127,597 A | 10/2000 | Beyar et al. |
| 6,136,011 A * | 10/2000 | Stambaugh .................. 606/159 |
| 6,140,452 A | 10/2000 | Felt et al. |
| 6,159,236 A | 12/2000 | Biel |
| 6,179,852 B1 | 1/2001 | Strickland et al. |
| 6,195,477 B1 | 2/2001 | Denuto et al. |
| 6,200,134 B1 | 3/2001 | Kovac et al. |
| 6,217,581 B1 | 4/2001 | Tolson |
| 6,223,085 B1 | 4/2001 | Dann et al. |
| 6,224,630 B1 | 5/2001 | Bao et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,258,089 B1 | 7/2001 | Campbell et al. |
| 6,261,289 B1 | 7/2001 | Levy |
| 6,280,456 B1 | 8/2001 | Scribner et al. |
| 6,282,013 B1 | 8/2001 | Ostler et al. |
| 6,290,382 B1 | 9/2001 | Bourn et al. |
| 6,299,597 B1 | 10/2001 | Buscemi et al. |
| 6,306,177 B1 | 10/2001 | Felt et al. |
| 6,319,255 B1 | 11/2001 | Grundei et al. |
| 6,332,894 B1 | 12/2001 | Stalcup et al. |
| 6,336,914 B1 | 1/2002 | Gillespie, III |
| 6,336,930 B1 | 1/2002 | Stalcup et al. |
| 6,358,252 B1 | 3/2002 | Shapira |
| 6,387,098 B1 | 5/2002 | Cole et al. |
| 6,395,007 B1 | 5/2002 | Bhatnagar et al. |
| 6,416,531 B2 | 7/2002 | Chen |
| 6,416,737 B1 | 7/2002 | Manolagas et al. |
| 6,419,483 B1 | 7/2002 | Adam et al. |
| 6,423,055 B1 | 7/2002 | Farr et al. |
| 6,423,083 B2 | 7/2002 | Reiley et al. |
| 6,425,923 B1 | 7/2002 | Stalcup et al. |
| 6,440,444 B2 | 8/2002 | Boyce et al. |
| 6,443,988 B2 | 9/2002 | Felt et al. |
| 6,447,514 B1 | 9/2002 | Stalcup et al. |
| 6,458,375 B1 | 10/2002 | Gertzman et al. |
| 6,478,751 B1 | 11/2002 | Krueger et al. |
| 6,482,234 B1 | 11/2002 | Weber et al. |
| 6,485,512 B1 | 11/2002 | Cheng |
| 6,494,883 B1 | 12/2002 | Ferree |
| 6,524,251 B2 | 2/2003 | Rabiner et al. |
| 6,524,313 B1 | 2/2003 | Fassier et al. |
| 6,551,321 B1 | 4/2003 | Burkinshaw et al. |
| 6,551,337 B1 | 4/2003 | Rabiner et al. |
| 6,565,528 B1 | 5/2003 | Mueller |
| 6,579,277 B1 | 6/2003 | Rabiner et al. |
| 6,579,279 B1 | 6/2003 | Rabiner et al. |
| 6,620,185 B1 | 9/2003 | Harvie et al. |
| 6,623,505 B2 | 9/2003 | Scribner et al. |
| 6,632,235 B2 * | 10/2003 | Weikel et al. ................. 606/192 |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Ranucci et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |

(56) References Cited

U.S. PATENT DOCUMENTS

| | | |
|---|---|---|
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,465,318 B2 | 12/2008 | Sennett et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim et al. |
| 8,210,729 B2 | 7/2012 | O'Leary et al. |
| 8,211,121 B1 | 7/2012 | Quinn et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,460 B2 | 5/2014 | Rabiner et al. |
| 8,764,761 B2 | 7/2014 | Truckai et al. |
| 8,870,965 B2 | 10/2014 | Rabiner et al. |
| 8,906,030 B2 | 12/2014 | Rabiner et al. |
| 8,906,031 B2 | 12/2014 | Rabiner et al. |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | DiPoto et al. |
| 9,005,254 B2 | 4/2015 | Rabiner et al. |
| 2001/0011174 A1 | 8/2001 | Reiley et al. |
| 2001/0044626 A1 | 11/2001 | Reiley et al. |
| 2002/0082600 A1 | 6/2002 | Shaolian et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |

(56) References Cited

U.S. PATENT DOCUMENTS

| | | |
|---|---|---|
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1 | 5/2007 | Shimizu et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0233146 A1 | 10/2007 | Henniges et al. |
| 2007/0239148 A1 | 10/2007 | Scheller |
| 2007/0255287 A1 | 11/2007 | Rabiner |
| 2008/0015500 A1 | 1/2008 | Herweck et al. |
| 2008/0019657 A1* | 1/2008 | Maitland et al. ............ 385/140 |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1* | 5/2008 | Rabiner et al. ................ 606/92 |
| 2008/0154266 A1* | 6/2008 | Protopsaltis et al. ........... 606/76 |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1* | 2/2009 | Rabiner et al. ................ 606/93 |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0082504 A1 | 4/2011 | Singhatt et al. |
| 2011/0098713 A1 | 4/2011 | Rabiner et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0137317 A1 | 6/2011 | O'Halloran et al. |
| 2011/0160870 A1 | 6/2011 | Baumgartner et al. |
| 2011/0166306 A1 | 7/2011 | Stansbury et al. |
| 2011/0313356 A1 | 12/2011 | Rabiner et al. |
| 2012/0029102 A1 | 2/2012 | Rose et al. |
| 2012/0041557 A1 | 2/2012 | Frigg |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO9943266 | 9/1999 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO2007002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/039811 | 4/2008 |
| WO | WO 2008/063265 | 5/2008 |
| WO | WO 2009/059090 | 5/2009 |
| WO | WO 2009/064847 | 5/2009 |
| WO | WO 2009/082688 | 7/2009 |
| WO | WO2009088927 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO2011162910 | 12/2011 |
| WO | WO2012051312 | 4/2012 |

(56) References Cited

FOREIGN PATENT DOCUMENTS

| WO | WO 2012/088432 | 6/2012 |
|----|----------------|--------|
| WO | WO 2013/013069 | 1/2013 |
| WO | WO 2013/013071 | 1/2013 |
| WO | WO 2013/013072 | 1/2013 |
| WO | WO2013/059609 | 4/2013 |
| WO | WO2014011669 | 1/2014 |
| WO | WO 2014/100427 | 6/2014 |

OTHER PUBLICATIONS

USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
USPTO Office Action in U.S. Appl. No. 13/617,557 mailed Oct. 9, 2013.
Extended European Search Report based on EP 10 76 2390 dated Oct. 30, 2013.
USPTO Office Action in U.S. Appl. No. 12/262,370 mailed Nov. 21, 2013.
PCT International Search Report based on PCT/US11/66871 dated May 1, 2012.
USPTO Office Action in U.S. Appl. No. 12/875,460 mailed Mar. 8, 2012.
USPTO Office Action in U.S. Appl. No. 11/964,370 mailed Mar. 16, 2012.
USPTO Office Action in U.S. Appl. No. 12/858,924 mailed Apr. 4, 2012.
USPTO Office Action in U.S. Appl. No. 12/756,014 mailed May 11, 2012.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/756,014 mailed Jan. 22, 2013.
USPTO Office Action in U.S. Appl. No. 13/088,916 mailed Jan. 23, 2013.
USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
USPTO Office Action in U.S. Appl. No. 13/553,247 mailed May 7, 2014.
Extended European Search Report based on EP 14156473 dated May 13, 2014.
USPTO Office Action in U.S. Appl. No. 13/800,518 mailed Jun. 10, 2014.
USPTO Office Action in U.S. Appl. No. 12/262,370 mailed Jun. 26, 2014.
USPTO Office Action in U.S. Appl. No. 13/617,557 mailed Jun. 27, 2014.
USPTO Office Action in U.S. Appl. No. 13/616,781 mailed Aug. 26, 2014.
USPTO Office Action in U.S. Appl. No. 13/730,521 mailed Sep. 8, 2014.
PCT International Search Report based on PCT/US13/049773 dated Oct. 1, 2013.
USPTO Office Action in U.S. Appl. No. 12/756,014 mailed Oct. 7, 2014.
USPTO Office Action in U.S. Appl. No. 13/553,450 mailed Oct. 24, 2014.
USPTO Office Action in U.S. Appl. No. 13/553,247 mailed Dec. 5, 2014.
USPTO Office Action in U.S. Appl. No. 13/553,051 mailed Dec. 23, 2014.
USPTO Office Action in U.S. Appl. No. 12/262,370 mailed Jan. 14, 2015.
USPTO Office Action in U.S. Appl. No. 13/617,557 mailed Jan. 15, 2015.
USPTO Office Action in U.S. Appl. No. 13/796,085 mailed Feb. 12, 2015.
Jovanovic et al., "Fixion Nails for Humeral Fractures, Injury", Int. J. Care Injured, vol. 35, Issue 11, pp. 1140-1142, Nov. 2004.
Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
PCT International Search Report based on PCT/US07/20402 dated Apr. 1, 2008.

(56) References Cited

OTHER PUBLICATIONS

PCT International Search Report based on PCT/US07/10050 dated Apr. 17, 2008.
PCT International Search Report based on PCT/US07/10038 dated Aug. 27, 2008.
PCT International Search Report based on PCT/US08/81929 dated Jan. 12, 2009.
PCT International Search Report based on PCT/US08/81924 dated Feb. 9, 2009.
PCT International Search Report based on PCT/US08/87630 dated Feb. 24, 2009.
PCT International Search Report based on PCT/US10/30275 dated Aug. 11, 2010.
PCT International Search Report based on PCT/US10/56219 dated Jan. 20, 2011.
PCT International Search Report based on PCT/US10/46003 dated May 24, 2011.
PCT International Search Report based on PCT/US11/38389 dated Sep. 22, 2011.
USPTO Office Action in U.S. Appl. No. 11/789,906 mailed Apr. 29, 2009.
USPTO Office Action in U.S. Appl. No. 11/789,906 mailed Mar. 11, 2010.
USPTO Office Action in U.S. Appl. No. 11/789,906 mailed Apr. 30, 2010.
USPTO Office Action in U.S. Appl. No. 11/789,907 mailed May 11, 2010.
USPTO Office Action in U.S. Appl. No. 11/903,123 mailed Jul. 1, 2010.
USPTO Office Action in U.S. Appl. No. 11/964,370 mailed Dec. 9, 2010.
USPTO Office Action in U.S. Appl. No. 11/964,370 mailed Apr. 28, 2011.
USPTO Office Action in U.S. Appl. No. 11/964,370 mailed Sep. 23, 2011.
USPTO Office Action in U.S. Appl. No. 12/262,411 mailed Sep. 1, 2010.
USPTO Office Action in U.S. Appl. No. 12/755,784 mailed Dec. 23, 2011.
USPTO Office Action in U.S. Appl. No. 12/858,924 mailed Oct. 24, 2011.
USPTO Office Action in U.S. Appl. No. 12/886,288 mailed Dec. 27, 2011.

\* cited by examiner

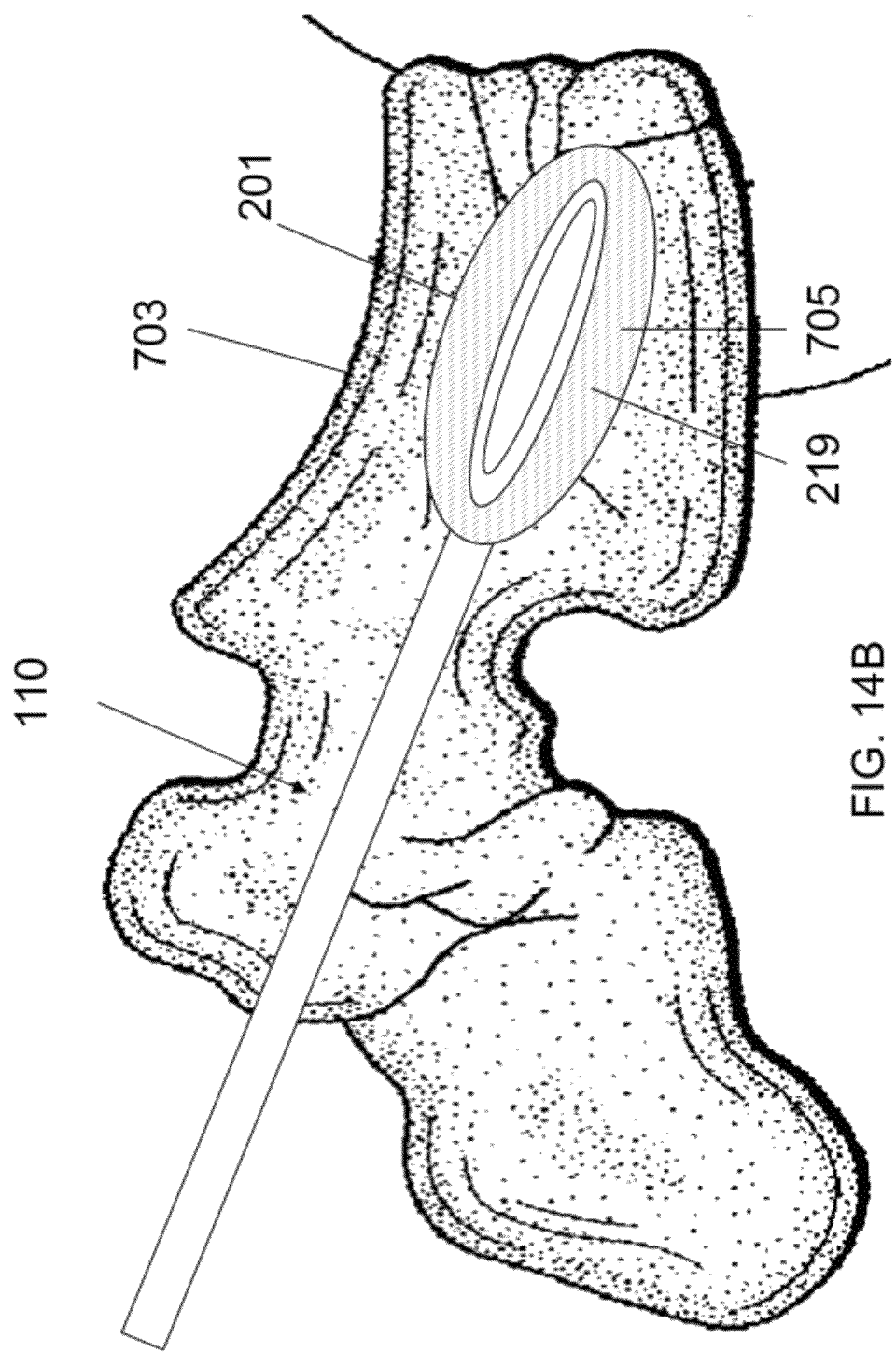

SYSTEMS AND METHODS FOR TREATING CONDITIONS AND DISEASES OF THE SPINE

RELATED APPLICATIONS

This application claims the benefit of U.S. Provisional Application Ser. No. 61/426,044, filed on Dec. 22, 2010, the entirety of this application is hereby incorporated herein by reference for the teachings therein.

FIELD

The embodiments disclosed herein relate to medical devices, and more particularly to systems and methods for treating conditions and diseases of the spine.

BACKGROUND

Degenerative disc disease (DDD) of the spine is one of the most common causes of lower back pain. The discs and the facet joints are considered the motion segments of the vertebral columns; the discs also act as shock absorbers between the vertebral bodies. Two prevalent causes of degenerative disc disease are increased thinning of the disc due to age, and thinning due to injury, for instance when the vertebral endplate tears from its connection to the intervertebral disc. Disc replacement goals include eliminating pain, sustaining range of motion, protecting adjacent spine segments, reducing morbidity and restoration of disc height.

Vertebral compression fractures are a common spinal injury. Such fractures happen when a vertebra collapses or is fractured due to trauma or due to a weakened vertebra in patients with osteoporosis, certain types of cancer or osteogenesis imperfecta, for example. When the vertebra collapses, the bone tissue on the inside is crushed or compressed, which can cause pain and spinal deformity. Vertebral compression fractures, if left untreated, may result in long term disability. Treatment goals include eliminating pain and restoration of disc height.

SUMMARY

Systems and methods for treating conditions and diseases of the spine are disclosed herein. According to aspects illustrated herein, there is provided a device that includes a balloon catheter having an elongated shaft with a proximal end, a distal end, and a longitudinal axis therebetween, the balloon catheter comprising at least one inner lumen incorporated within the elongated shaft; an inner balloon positioned inside and completely surrounded by an outer balloon, the balloons located at the distal end; and an adapter for passage of at least one of an inflation fluid or a medical instrument, the adapter located at the proximal end; and an optical fiber having a core surrounded by a cladding material, the optical fiber comprising an outer diameter sized to pass through the inner lumen of the elongated shaft of the balloon catheter; a nonlinear light-emitting portion of a given length, wherein a portion of the cladding material from the nonlinear light-emitting portion has been removed so that light energy may be emitted along the length of the nonlinear light-emitting portion; and a linear elongated portion for guiding light towards the nonlinear light-emitting portion.

According to aspects illustrated herein, there is provided a device that includes a balloon catheter having an elongated shaft with a proximal end, a distal end, and a longitudinal axis therebetween; an expandable member releasably disposed at a distal end of the balloon catheter, the expandable member comprising an outer balloon and one or more inner balloons; and an optical fiber having a pre-shaped distal portion, wherein the balloon catheter includes a plurality of inner lumens in fluid communication with a plurality of inner cavities within the expandable member for passing the optical fiber, an inflation fluid, and a light-sensitive fluid to the plurality of inner cavities within the expandable member, and wherein the optical fiber is configured to emit light along at least a part of the pre-shaped distal portion of the optical fiber.

According to aspects illustrated herein, there is provided a system that includes a balloon catheter having an elongated shaft with a proximal end, a distal end, and a longitudinal axis therebetween, the balloon catheter comprising at least one inner lumen incorporated within the elongated shaft; at least a first inner inflatable balloon positioned inside and completely surrounded by an outer inflatable balloon, the balloons located at the distal end; and an adapter for passage of at least one of an inflation fluid or a medical instrument, the adapter located at the proximal end; an optical fiber having a core surrounded by a cladding material, the optical fiber comprising an outer diameter sized to pass through the inner lumen of the elongated shaft of the balloon catheter; a nonlinear light-emitting portion of a given length, wherein a portion of the cladding material from the nonlinear light-emitting portion has been removed so that light energy may be emitted along the length of the nonlinear light-emitting portion; a linear elongated portion for guiding light towards the nonlinear light-emitting portion; a relaxed condition in which the nonlinear light-emitting portion of the optical fiber assumes a curved conformation; a stretched condition in which the nonlinear light-emitting portion of the optical fiber has a linear conformation in which the nonlinear light-emitting portion of the optical fiber can be advanced through the inner lumen of the elongated shaft of the balloon catheter; and a memory which returns the nonlinear light-emitting portion from the stretched condition to the relaxed condition; a light-sensitive fluid; and a light source.

According to aspects illustrated herein, there is provided a method for repairing a vertebral compression fracture that includes gaining access to a collapsed vertebrae; delivering to the collapsed vertebrae, in an unexpanded state, an expandable member having a inner balloon positioned inside and completely surrounded by an outer balloon; injecting an inflation fluid into the outer balloon to expand the outer balloon and to temporarily restore height of the collapsed vertebrae; maintaining the expanded outer balloon while injecting a light-sensitive fluid into the inner balloon to expand the inner balloon within the expanded outer balloon; positioning an optical fiber sufficiently designed to emit light energy along a length of the optical fiber inside the expandable member, wherein the optical fiber is connected to a light source; activating the light source; delivering light energy to the optical fiber from the light source; and curing the light-sensitive fluid inside the inner balloon to harden the inner balloon within the expanded outer balloon.

According to aspects illustrated herein, there is provided a method for repairing a vertebral compression fracture that includes positioning an expandable member releasably disposed at a distal end of a balloon catheter within a cancellous bone region of a fractured or collapsed vertebra, wherein the expandable member comprises an outer balloon and one or more inner balloons; moving the outer balloon from a deflated state to an inflated state to expand the collapsed or fractured vertebra to a desired height; moving one or more inner balloons from a deflated state to an inflated state with a light-sensitive fluid; introducing a pre-shaped optical fiber into an inner cavity within the outer balloon; activating the optical fiber to uniformly cure the light-sensitive fluid within the one or more inner balloons; moving the outer balloon from the inflated state to the deflated state; and releasing the expandable member from the balloon catheter.

According to aspects illustrated herein, there is provided a method for replacing a degenerative disc that includes removing a degenerative disc to create a space; delivering to the space, in an unexpanded state, an expandable member having at least a first inner balloon positioned inside and completely surrounded by an outer balloon; injecting an inflation fluid into the outer balloon to expand the outer balloon and to temporarily restore native disc height; maintaining the expanded outer balloon while injecting a light-curable fluid into the first inner balloon to expand the first inner balloon within the expanded outer balloon; positioning an optical fiber sufficiently designed to emit light energy along a length of the optical fiber inside the expandable member, wherein the optical fiber is connected to a light source; activating the light source; delivering light energy to the optical fiber from the light source; and curing the light-curable fluid inside the first inner balloon to harden the first inner balloon within the expanded outer balloon.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 14A-14E show an embodiment of method steps for repairing a vertebral compression fracture using components of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

A medical device disclosed herein may be used for treating conditions and diseases of the spine, including, but not limited to, vertebral compression fractures (repairing bones) and degenerative disc disease (repairing soft tissue) resulting from osteoporosis, pressure on the spine, metastatic disease, or a fall or other type of injury. Although the medical devices disclosed herein are contemplated to be used for treating such spine conditions and diseases, those skilled in the art will recognize that the disclosed devices and methods may be used for repairing other bones including, but not limited to, the femur, tibia, fibula, humerus, ulna, radius, metatarsals, phalanx, phalanges, ribs, spine, vertebrae, clavicle and other bones and still be within the scope and spirit of the disclosed embodiments.

Figure 1:
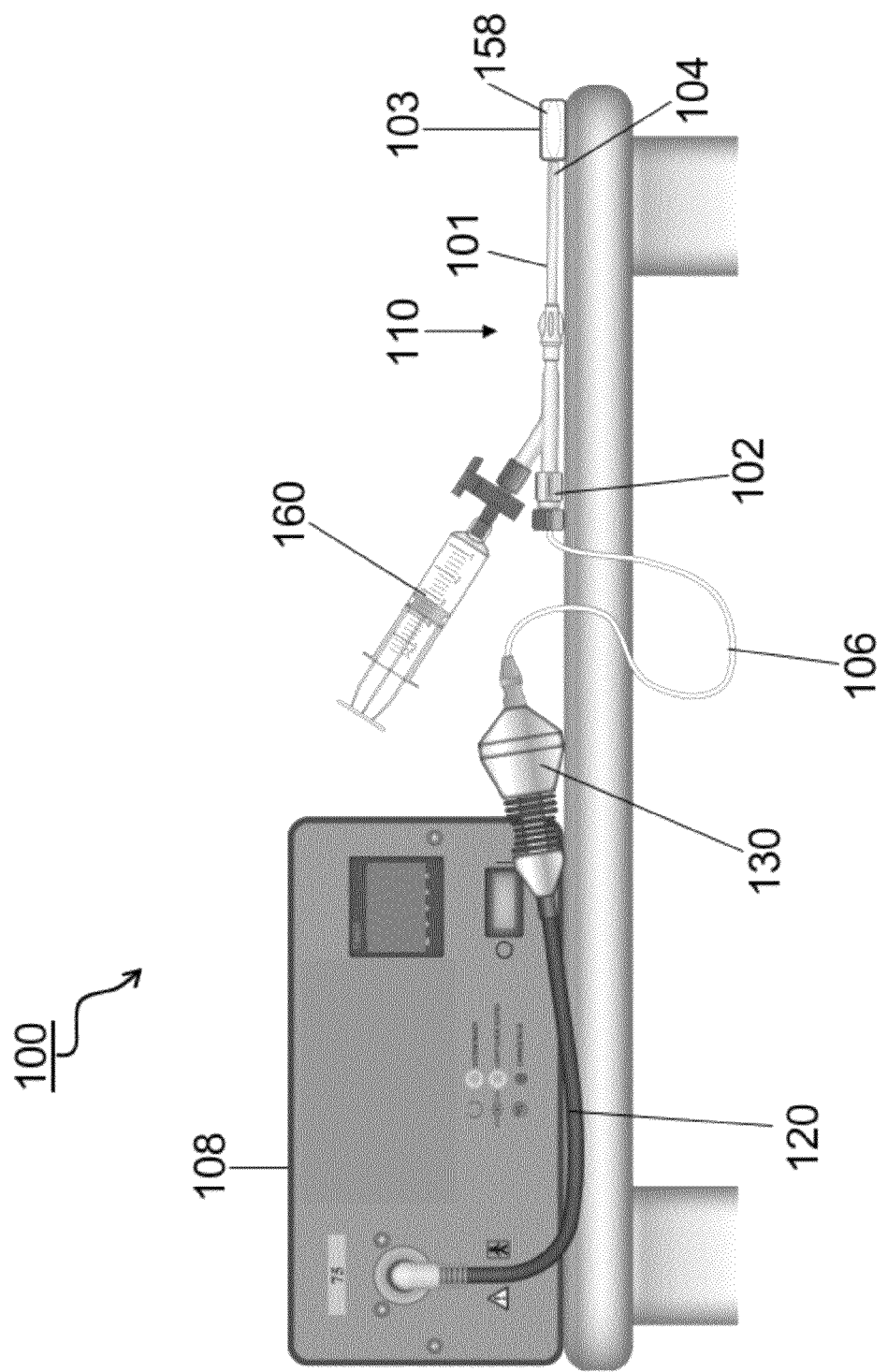
FIG. 1 is a schematic illustration showing various components of an embodiment of a system of the present disclosure.

FIG. 1 is a schematic illustration showing various components of an embodiment of a system 100 of the present disclosure. System 100 includes a light source 108, a light pipe 120, an attachment system 130 and a light-conducting optical fiber 106 having a nonlinear light-emitting portion 158, which emits light from the outside of the optical fiber 106 along its length. The attachment system 130 communicates light energy from the light source 108 to the optical fiber 106. In an embodiment, the light source 108 emits frequency that corresponds to a band in the vicinity of 390 nm to 770 nm, the visible spectrum. In an embodiment, the light source 108 emits frequency that corresponds to a band in the vicinity of 410 nm to 500 nm. In an embodiment, the light source 108 emits frequency that corresponds to a band in the vicinity of 430 nm to 450 nm. The optical fiber 106 can be made from any material, such as glass, silicon, silica glass, quartz, sapphire, plastic, combinations of materials, or any other material, and may have any diameter. In an embodiment, the optical fiber 106 is made from a polymethyl methacrylate core with a transparent polymer cladding. It should be noted that the term "optical fiber" is not intended to be limited to a single optical fiber, but may also refer to multiple optical fibers as well as other means for communicating light from the light source to the expandable member.

System 100 further includes a balloon catheter 110 having an elongated shaft 101 with a proximal end 102, a distal end 104, and a longitudinal axis therebetween. In an embodiment, the balloon catheter 110 has an outside diameter ranging from about 3 mm (9 French) to about 8 mm (24 French). In an embodiment, the balloon catheter 110 may have an outside diameter of about 3 mm (9 French). At least one inner lumen is incorporated within the elongated shaft 101 of the balloon catheter 110. In an embodiment, the elongated shaft 101 of the balloon catheter 110 includes two inner lumens. In an embodiment, the elongated shaft 101 of the balloon catheter 110 includes three inner lumens. The proximal end 102 of the balloon catheter 110 includes an adapter for passage of at least one of inflation fluids or medical instruments, as will be described with respect to FIG. 2. The distal end 104 of the balloon catheter 110 includes at least a first inner inflatable balloon positioned inside and completely surrounded by an outer inflatable balloon, and is generally shown as expandable member 103. In an embodiment, the expandable member 103 is manufactured from a non-compliant (non-stretch/non-expansion) conformable material. In an embodiment, the expandable member 103 is manufactured from a conformable compliant material that is limited in dimensional change by embedded fibers. One or more radiopaque markers, bands or beads may be placed at various locations along the expandable member 103 and/or the balloon catheter 110 so that components of the system 100 may be viewed using fluoroscopy.

Figure 2:
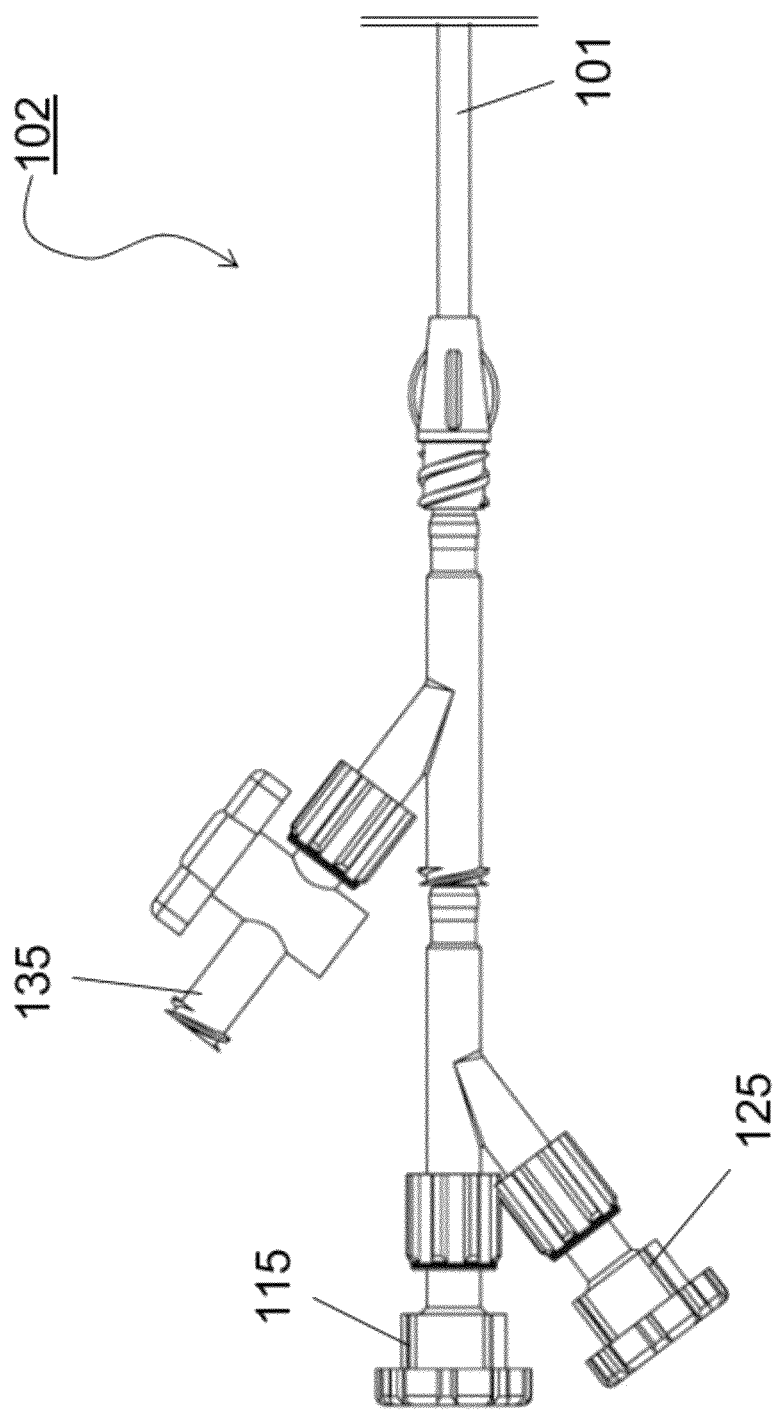
FIG. 2 is a side view of an embodiment of a proximal end of a balloon catheter of the present disclosure.

FIG. 2 is a side view of an embodiment of a proximal end of a balloon catheter of the present disclosure. Referring to FIG. 2, in an embodiment, the proximal end 102 of the balloon catheter 110 may include a multipurpose adapter having multiple ports 115, 125, and 135 configured to accept inflation fluids or medical instruments to be delivered through the balloon catheter 110 towards (and/or into) the expandable member 103. In an embodiment, a manifold may be provided that can be connected to a port, the manifold including multiple ports and indicia to remind a user which one of the balloons is controlled through which port. One of the ports can accept, for example, the optical fiber 106. The other port can accept, for example, a syringe 160 housing a light-sensitive fluid (see, for example, FIG. 1). In an embodiment, the syringe 160 maintains a low pressure during the infusion and aspiration of the light-sensitive fluid. In an embodiment, the syringe 160 maintains a low pressure of about 10 atmospheres or less during the infusion and aspiration of the light-sensitive fluid.

Expandable Member

The distal end of the balloon catheter includes an expandable member having at least a first inflatable balloon positioned inside and completely surrounded by an outer inflatable balloon. In an embodiment, the external surface of any of the balloons is resilient and puncture resistant. In an embodiment, the external surface of any of the balloons is free of pores and does not allow for inflation fluid to escape from the balloon. In an embodiment, a balloon of the present disclosure is a high-pressure balloon molded to an inflated geometry from noncompliant or low-compliant materials that retain their designed size and shape even under high pressure. In an embodiment, a balloon of the present disclosure is thin walled and exhibits high tensile strength, with relatively low elongation. In an embodiment, because an outer inflatable balloon may need to be pressurized to a higher pressure than an inner inflatable balloon, the outer inflatable balloon may have a thicker wall and/or be made of stronger material than the inner inflatable balloon(s). In an embodiment, the balloons are manufactured from a non-compliant (non-stretch/non-expansion) conformable material including but not limited to urethane, polyethylene terephthalate (PET), nylon elastomer and other similar polymers. In an embodiment, the balloons are manufactured from a polyethylene terephthalate (PET) and are optically clear and can transmit light over a broad spectrum. In an embodiment, the balloons of the present disclosure have a size ranging from about 0.5 to about 50 mm in diameter in virtually any working length. In an embodiment, the balloons are manufactured from a radiolucent material, which permit x-rays to pass through the balloons. In an embodiment, the balloons are manufactured from a radiolucent polyethylene terephthalate (PET). In an embodiment, the balloons are manufactured from a conformable compliant material that is limited in dimensional change by embedded fibers.

One or more radiopaque markers or bands may be placed at various locations along one or more balloons of the plurality of the balloons. A radiopaque ink bead may be placed at the distal end of the expandable member for alignment of the balloon catheter and/or the expandable member during fluoroscopy. The one or more radiopaque bands, using radiopaque materials such as barium sulfate, tantalum, or other materials known to increase radiopacity, may allow a medical professional to view the balloon catheter and/or the expandable member using fluoroscopy techniques. The one or more radiopaque bands may also provide visibility during inflation of the balloons of the expandable member to determine the precise positioning of the balloons and the device during placement and inflation. The one or more radiopaque bands may also permit visualization of any voids that may be created by air that gets entrapped in the balloons.

In an embodiment, at least a portion of the external surface of a balloon is substantially even and smooth. Alternatively or additionally, in an embodiment, an outer surface of a balloon may be textured or roughened to further promote tissue adhesion to the expandable member. In an embodiment, at least a portion of the external surface of the balloon includes at least one textured element such as a bump, a ridge, a rib, an indentation or any other shape. In an embodiment, the textured element may enhance the attachment of bone, cell, or tissue to the balloon. In an embodiment, at least a portion of the external surface of the balloon protrudes out to form a textured element. In an embodiment, at least a portion of the external surface of the balloon invaginates to form a textured element. In an embodiment, the textured element increases the friction and improves the grip and stability of the balloon after the balloon is inserted. In an embodiment, the textured element results in increased interdigitation of bone-device interface as compared to a balloon without textured elements. In an embodiment, the textured element can be convex in shape. In an embodiment, the textured element can be concave in shape. In an embodiment, the textured element can be circumferential around the width of the balloon, either completely or partially.

In general, bone graft or bone graft substitute can be used in conjunction with a balloon of the present disclosure. In an embodiment, the bone graft is an allogeneic bone graft. In an embodiment, the bone graft is an autologous bone graft. In an embodiment, the bone graft substitute is a hydroxyapatite bone substitute. In an embodiment, a bone graft or bone graft substitute is used to fill in any gaps that may exist, for example, between the external surface of the balloon and the surfaces of the bone fragments. In an embodiment, a bone graft or bone graft substitute is used to fill any gaps that may exist, for example, between the textured element of the balloon and the surfaces of the bone fragments.

In general, a balloon can include an external surface that may be coated with materials including, but not limited to, drugs (for example, antibiotics), proteins (for example, growth factors) or other natural or synthetic additives (for example, radiopaque or ultrasonically active materials). For example, after a minimally invasive surgical procedure an infection may develop in a patient, requiring the patient to undergo antibiotic treatment. An antibiotic drug may be added to the external surface of a balloon to prevent or combat a possible infection. Proteins, such as, for example, bone morphogenic protein or other growth factors have been shown to induce the formation of cartilage and bone. A growth factor may be added to the external surface of a balloon to help induce the formation of new bone. Due to the lack of thermal egress of the light-sensitive liquid monomer in a balloon, the effectiveness and stability of the coating is maintained.

In an embodiment, at least one bearing surface of a balloon may be covered with a biocompatible material. In an embodiment, the biocompatible material may be an expanded biocompatible material such as polytetrafluoroethylene (PTFE). The biocompatible material may provide both a surface and a compressive material that can absorb any abrasive contact with sharpened surfaces of a bone to be stabilized. In an embodiment, at least one bearing surface of a balloon may be covered with a thickened PTFE capable of transiting sharp surfaces and modulating them into curves that would not be potentially disruptive to the plurality of balloons.

In general, a balloon typically does not have any valves. One benefit of having no valves is that the balloon may be expanded or reduced in size as many times as necessary to assist in the fracture reduction and placement. Another benefit of the balloon having no valves is the efficacy and safety of the system. Since there is no communication passage of light-sensitive liquid monomer to the body there cannot be any leakage of liquid monomer because all the liquid monomer is contained within the balloon. In an embodiment, a permanent seal is created between the balloon and the balloon catheter that is both hardened and affixed prior to the balloon catheter being removed.

In an embodiment, abrasively treating the external surface of a balloon for example, by chemical etching or air propelled abrasive media, improves the connection and adhesion between the external surface of the balloon and a bone surface. The surfacing significantly increases the amount of surface area that comes in contact with the bone which can result in a stronger grip.

In general, a balloon of the present disclosure can include any of the features described above, with modification to some or all of the features.

Figure 3:
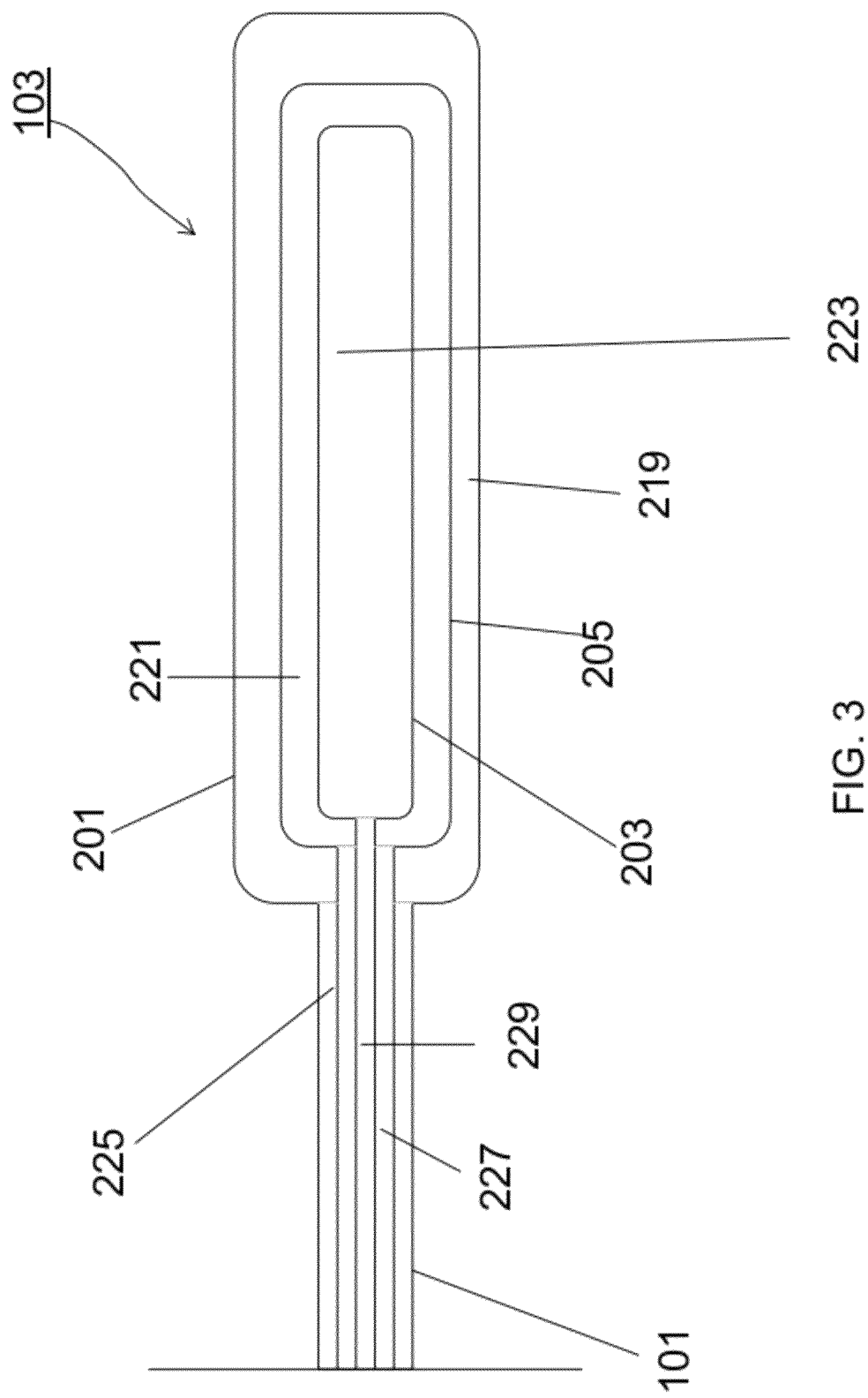
FIG. 3 is a side view of an embodiment of a distal end of a balloon catheter of the present disclosure.

FIG. 3 is a side view of an embodiment of a distal end 104 of a balloon catheter 110 of the present disclosure. The distal end 104 of the balloon catheter 110 terminates in an expandable member 103 comprising at least two balloons. In an embodiment, the at least two balloons are concentric relative to one another. The expandable member 103 comprises an outer expandable balloon 201 and one or more inner expandable balloons 203 and 205. For the sake of clarity, the balloon 203 may be referred to herein as the inmost inner balloon 203 and the balloon 205 may be referred to herein as the intermediate inner balloon 205. It should be understood that although the device illustrated in FIG. 3 includes two inner balloons 203 and 205, a device of the present disclosure may alternatively include only one inner balloon (as illustrated, for example, in FIG. 10, FIG. 11, FIG. 12 and FIG. 13) or more than two inner balloons as desired. Each balloon may be moved from a deflated state to an inflated state, as will be described below, independently of other balloons. It should be noted that operating, i.e., inflating or deflating, one or more of the inner balloons may also at least partially operate other balloons, especially balloons that are outer to the balloon being operated.

In an embodiment, one or more of the inner balloons may include a pressure relief valve. In operation, if the pressure inside a balloon having a pressure relief valve exceeds a pre-established limit, such as due to the user's error or the patient's movement, the pressure relief valve may release some of the fluid in the balloon into an adjacent balloon to decrease the pressure below the pre-established limit.

In an embodiment, each balloon may be a specific shape demanded, for example, by the anatomical site including, but not limited to, round, flat, cylindrical, dog bone, tapered, oval, conical, spherical, square, rectangular, toroidal and combinations thereof, independently of other balloons. Each balloon may be positioned in any orientation relative to the catheter, independently of other balloons.

In an embodiment, a separation area is located at the junction between the expandable member and the balloon catheter. The separation area may have a stress concentrator. The stress concentrator may be a notch, groove, channel or similar structure that concentrates stress in the separation area. The stress concentrator of the separation area may be notched, scored, indented, pre-weakened or pre-stressed to direct separation of the expandable member from the elongated shaft of the balloon catheter under specific torsional and/or tension load. The separation area ensures that there are no leaks of the light-sensitive fluid from the balloon catheter and/or the expandable member. The separation area seals the expandable member and removes the balloon catheter by making a break at a known or predetermined site (e.g., a separation area). The separation area may be various lengths and up to about an inch long. In an embodiment, when torque (twisting) is applied to the balloon catheter the elongated shaft of the balloon catheter separates from the expandable member. The twisting creates a sufficient shear to break the residual hardened light-sensitive liquid monomer (now a polymer) and create a clean separation of the expandable member/balloon catheter interface. In an embodiment, the expandable member may be separated from the balloon catheter using a separation instrument. The separation area may have a defined position for a separation instrument to engage the balloon catheter. The position of the separation area on the balloon catheter may not only be marked and identified by a radiopaque marker band, but there may be a physical step in the balloon catheter to provide both a tactile and audible feel and sound to the user to identify the delivery and positioning of the separation tool. The combination of these two aspects may decrease the dependence of fluoroscopy imaging and exposure to both the patient and the surgeon. In yet another embodiment, the expandable member may be cut from the balloon catheter using a cutting device.

Figure 4:
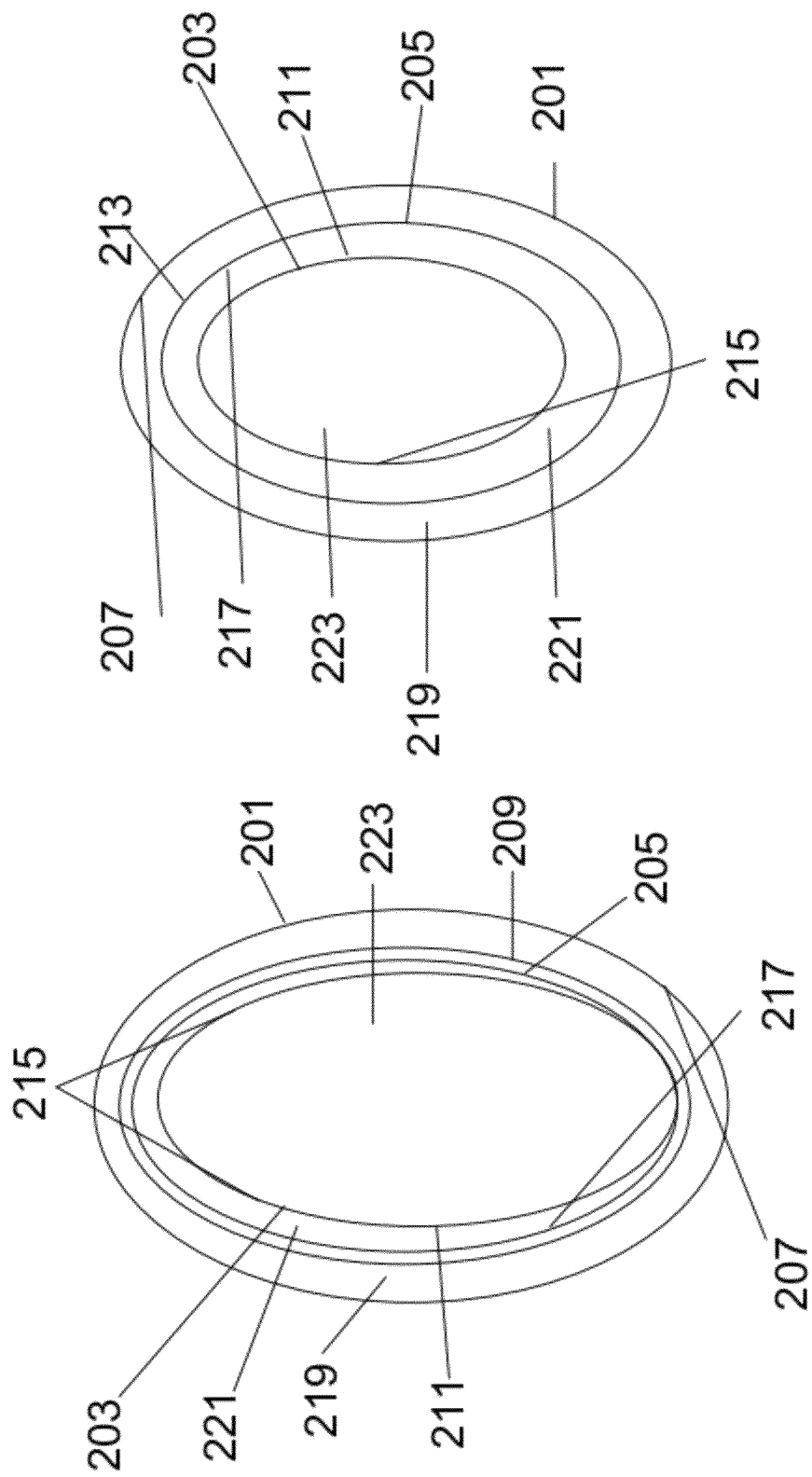
FIG. 4A and FIG. 4B are cross-sectional views of embodiments of expandable members of a balloon catheter of the present disclosure.

In an embodiment, at least one of the balloons may be toroidal in shape, with the walls of the balloon defining an inner cavity within the balloon. For example, FIG. 4A is a cross-sectional view of an embodiment of the expandable member 103 comprising an outer balloon 201 having a toroidal shape, and intermediate inner balloon 205 and inmost inner balloon 203 having an oval shape. In the embodiment shown in FIG. 4A, the outer balloon 201 is in a vertical orientation, i.e., with flat sides forming the top and bottom surfaces of the outer balloon 201. It should be understood, however, that the outer balloon 201 could also be positioned in a horizontal orientation, i.e., with flat sides forming the proximal and distal surfaces of the outer balloon 201. In an embodiment, the outer balloon 201 and the inner balloons 203 and 205 each are in fluid communication with an inflation fluid or light-sensitive fluid by virtue of an inner lumen of the balloon catheter 110. In an embodiment, the outer balloon 201 is in fluid communication with an inflation fluid or light-sensitive fluid 165 that is distinct from an inner lumen of the balloon catheter 110. An outmost inner cavity 219 is defined by inner surfaces 207 and 209 of the outer balloon 201. An intermediate inner cavity 221 may be formed between an inner surface 217 of the intermediate inner balloon 205 and an outer surface 211 of the inmost inner balloon 203. An inmost inner cavity 223 may defined by an inner surface 215 of the inner balloon 203. In an embodiment, the intermediate inner balloon 205 may serve as a protective barrier to contain the polymerized light-sensitive fluid within the inmost inner balloon 203 in case the inmost inner balloon 203 ruptures or leaks. Additionally or alternatively, a seal may be provided over the central hole of the toroidal outer balloon 201 to provide further protection in case the inmost inner balloon 203 having the light-sensitive fluid ruptures or leaks.

In an embodiment, a plurality of inner cavities may be defined by the plurality of balloons of the expandable member 103. For example, FIG. 4B is a cross-sectional view of an embodiment of an expandable member 103 comprising an outer balloon 201, an inmost inner balloon 203, and an intermediate inner balloon 205, with the balloons 201, 203, 205 having an oval shape. An outmost inner cavity 219 may be formed between the inner surface 207 of the outer balloon 201 and an outer surface 213 of the intermediate inner balloon 205. Moreover, an intermediate inner cavity 221 may be formed between the inner surface 217 of the intermediate inner balloon 205 and the outer surface 211 of the inmost inner balloon 203. Finally, an inmost inner cavity 223 may be defined by the inner surface 215 of the inmost inner balloon 203. Throughout the specification, a wall of an inner cavity closest to the outside of the expandable member 103 will be referred to herein as an outer wall and a wall of an inner cavity farthest from the outside of the expandable member 103 will be referred to herein as an inner wall. For example, in reference to FIG. 3, the outmost inner cavity 219 includes an outer wall 201 and an inner wall 205.

Each inner cavity of the plurality of inner cavities is in fluid communication with one or more inner lumens incorporated within the elongated shaft of the balloon catheter. A balloon may be moved from a deflated state to an inflated state by injecting an inflation fluid into one or more inner cavities within the balloon via one or more corresponding inner lumens. The term "inflation fluid" refers to any fluid that can be used to expand a balloon to a desired pressure and/or height. Suitable inflation fluids, include but are not limited to, liquids, such as, water, saline and light-sensitive fluid, or gasses, such as nitrogen and air, or combinations thereof.

In reference to FIG. 3, in an embodiment, the outmost inner cavity 219 may be in fluid communication with an outmost lumen 225; the intermediate inner cavity 221 may be in fluid communication with an intermediate lumen 227; and the inmost inner cavity 223 may be in communication with an inmost lumen 229. In an embodiment, at least one of the outmost lumen 225, the intermediate lumen 227 or the inmost lumen 229 has a diameter ranging from about 1.0 mm to about 4.0 mm. In an embodiment, the outer balloon 201 may be moved from a deflated state to an inflated state by injecting an inflation fluid into the outmost inner cavity 219 via the outmost lumen 225. The intermediate inner balloon 205 may be moved from a deflated state to an inflated state by injecting an inflation fluid into the intermediate inner cavity 221 via the intermediate lumen 227. The inmost inner balloon 203 may be moved from a deflated state to an inflated state by injecting an inflation fluid into the inmost inner cavity 223 via the inmost lumen 229. The balloons 201, 203, 205 may be moved from an inflated state to a deflated state by withdrawing an inflation fluid from the inner cavities 219, 223, 221. It should be noted that although as illustrated the number of lumens correspond to the number of inner cavities, the number of lumens may be more or fewer than the number of inner cavities. In other words, in an embodiment, a single inner cavity may be in fluid communication with multiple lumens and/or a single lumen may be in fluid communication with multiple inner cavities.

In an embodiment, the intermediate inner cavity 221 and the inmost cavity 223 may be filled with the same light-sensitive fluid. In another embodiment, the intermediate inner cavity 221 and the inmost cavity 223 may be filled with different light-sensitive fluids having different shore hardness so the inner balloons 203 and 205 may have different physical characteristics when the light-sensitive fluid is cured. Accordingly, an implant formed from the expandable member 103 can be a layered implant with layers having different physical characteristics, such as, for example, hardness, flexibility, and elasticity.

As noted, the optical fiber communicating light from the light source can be introduced through an inner lumen incorporated within the elongated shaft of the balloon catheter into the expandable member to activate the light-sensitive liquid monomer and cause it to cure. For example, to cure the light-sensitive fluid inside the inmost inner cavity 223 of the inmost inner balloon 203, an optical fiber 106 may be positioned either in the outmost inner cavity 219 the intermediate inner cavity 221 so as to result in a cure that initiates from outside the inmost inner cavity 223 into the inmost inner cavity 223. In an embodiment, to cure the light-sensitive fluid inside the intermediate inner cavity 221, an optical fiber 106 may be positioned in the outmost inner cavity 219 so as to result in a cure that initiates from outside the intermediate inner cavity 221 into the intermediate inner cavity 221. In an embodiment, to cure the light-sensitive fluid inside the outmost inner cavity 219, an optical fiber 106 may be positioned in the outmost inner cavity 219 so as to result in a cure that initiates from inside of the outmost inner cavity 219 out of the outmost inner cavity 219.

Light-Sensitive Fluid

A photodynamic light-sensitive fluid may be of liquid consistency during storage and delivery to the expandable member, but may be cured, i.e., solidified or hardened, by exposing the light-sensitive fluid to light, such as from the optical fiber from inside the expandable member. In an embodiment, the light-sensitive fluid is a photodynamic (light-curable) liquid monomer with photoinitiator. The light-sensitive liquid monomer with photoinitiator is exposed to an appropriate frequency of light and intensity to cure the monomer inside the expandable member and form a rigid structure. The addition of the light causes a fragmentation of the photoinitiator, which initiates the polymerization process: monomers and oligomers join together to form a durable biocompatible crosslinked polymer.

In an embodiment, the light-sensitive fluid is exposed to an appropriate frequency of light and intensity to cure the monomer inside the expandable balloon and form a rigid structure. In an embodiment, the light-sensitive fluid is exposed to electromagnetic spectrum that is visible (frequency that corresponds to a band in the vicinity of 390 nm to 770 nm). In an embodiment, the light-sensitive fluid is exposed to electromagnetic spectrum with a frequency that corresponds to a band in the vicinity of 400 nm to 500 nm). In an embodiment, the light-sensitive fluid is radiolucent, which permit x-rays to pass through the light-sensitive fluid. The term "cure" may refer to any chemical, physical, and/or mechanical transformation that allows a composition to progress from a form (e.g., flowable form) that allows it to be delivered through an inner lumen of the balloon catheter, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components). In an embodiment, the light-sensitive fluid is radiolucent, which permit x-rays to pass through the light-sensitive fluid.

In an embodiment, the viscosity of the light-sensitive fluid is from about 1000 cP or less. In an embodiment, the light-sensitive fluid has a viscosity ranging from about 650 cP to about 450 cP. The inflatable balloons may be inflated, trial fit and adjusted as many times as a user wants with the light-sensitive fluid, up until the light source is activated, when the polymerization process is initiated. Because the light-sensitive fluid has a liquid consistency and is viscous, the light-sensitive fluid may be delivered using low pressure delivery and high pressure delivery is not required, but may be used. A low pressure system may also be adequate to deliver the light-sensitive fluid because the light-sensitive fluid will most often be used to inflate an inner balloon to fill in an empty space previously created by the outer balloon so there will be no or very little backpressure on the light-sensitive fluid.

In an embodiment, the light-sensitive fluid may be provided as a unit dose. As used herein, the term "unit dose" is intended to mean an effective amount of light-sensitive fluid adequate for a single session. By way of a non-limiting example, a unit dose of a light-sensitive fluid of the present disclosure for expanding the one or more inner balloons may be defined as enough light-sensitive fluid to expand the one or more inner balloons so that the expanded one or more inner balloons substantially fill the space created by the outer balloon. The volume of space created by the outer balloon may vary somewhat from user to user. Thus, a user using a unit dose may have excess light-sensitive fluid left over. It is desirable to provide enough light-sensitive fluid that even the above-average user will have an effective amount of height restoration. In an embodiment, a unit dose of a light-sensitive fluid of the present disclosure is contained within a container. In an embodiment, a unit dose of a light-sensitive fluid of the present disclosure is contained in an ampoule. In an embodiment, a unit dose of a light-sensitive fluid of the present disclosure is contained in a syringe. In an embodiment, the light-sensitive fluid can be delivered under low pressure via a syringe attached to the port. The light-sensitive fluid can be aspirated and re-infused as necessary, allowing for adjustments to the inmost inner balloon or the intermediate inner balloon. These properties allow a user to achieve maximum fracture reduction prior to activating a light source and converting the liquid monomer into a hard polymer. Additives may be included in the light-sensitive fluid and/or inflation fluid, including, but not limited to, drugs (for example, antibiotics), proteins (for example, growth factors) or other natural or synthetic additives (for example, radiopaque or ultrasonically active materials).

In an embodiment, an optical fiber or the present disclosure is connected to a light source that emits frequency corresponding to a band in the vicinity of 390 nm to 770 nm, the visible spectrum. In an embodiment, the light source emits frequency that corresponds to a band in the vicinity of 410 nm to 500 nm. In an embodiment, the light source emits frequency that corresponds to a band in the vicinity of 430 nm to 450 nm. The light-sensitive fluid remains a liquid monomer until activated by the light where the light meets the monomer and polymerizes the monomer (cures on demand). In an embodiment, the light-sensitive fluid is exposed to an appropriate frequency of light and intensity to cure the monomer inside an expandable balloon and form a rigid structure. In an embodiment, the light-sensitive fluid is radiolucent, which permit x-rays to pass through the liquid monomer. Radiant energy from the light source is absorbed and converted to chemical energy to quickly (e.g., cured in about five seconds to about five minutes) polymerize the monomer. This cure affixes an inner balloon in an inflated state.

In an embodiment, a contrast material may be added to the light-sensitive fluid and/or inflation fluid without significantly increasing the viscosity. Contrast materials include, but are not limited to, barium sulfate, tantalum, or other contrast materials known in the art. The light-sensitive fluid can be aspirated and re-infused as necessary, allowing for thickness adjustments to the one or more inner balloons prior to activating the light source and converting the liquid monomer into a hard polymer. Low viscosity allows filling of the one or more inner balloons through a very small delivery system.

In an embodiment, the light-sensitive fluid of the present disclosure is a liquid monomer with photoinitiator that has a viscosity ranging from about 650 cP to about 450 cP, wherein exposure to light energy having a wavelength of 430 nm to 450 nm causes the light-sensitive fluid to cure.

Optical Fiber

An optical fiber uses a construction of concentric layers for optical and mechanical advantages. The most basic function of a fiber is to guide light, i.e., to keep light concentrated over longer propagation distances—despite the natural tendency of light beams to diverge. In the simple case of a step-index fiber, this guidance is achieved by creating a region with increased refractive index around the fiber axis, called the fiber core, which is surrounded by the cladding material. The cladding material may be protected with a polymer coating. Light is kept in the "core" of the optical fiber by total internal reflection. Cladding keeps light traveling down the length of the fiber to a destination.

An optical fiber of the present disclosure is sized to pass through an inner lumen of the elongated shaft of the balloon catheter. In an embodiment, the optical fiber has an outer diameter ranging from about 1 mm to about 4 mm. In an embodiment, the optical fiber has an outer diameter between about 0.75 mm to about 2.0 mm. In an embodiment, the optical fiber has an outer diameter between about 1.0 mm and about 1.5 mm. The outer diameter of the optical fiber refers to the core plus the cladding plus any additional buffers or jackets that may be present.

In an optical fiber of the present disclosure, it is desirable to extract (emit) light along a given length of the optical fiber rather than only at the optical fiber's terminating face (distal tip). An optical fiber of the present disclosure includes a light-emitting portion of a given length, wherein a portion of the cladding material from the light-emitting portion has been removed so that light energy may be dispersed along the length of the light-emitting portion. Thus, at least a portion of a length of the optical fiber has been modified, e.g., by removing some of the cladding material, in order to alter the direction, propagation, amount, intensity, angle of incidence, uniformity and/or distribution of light. In an embodiment, the dispersion of light energy from the light-emitting portion occurs in a radial direction.

In an embodiment, at least a portion of a length of the optical fiber has been modified by cutting or notching the cladding material to create the light-emitting portion of the optical fiber. In an embodiment, the light-emitting portion has been created by forming a helical design along a length of the optical fiber. Such a design may be created by applying a spiral cutter used to cut away cladding material in a helical profile around the optical fiber. While some embodiments may include continuous variations in the frequency of the cut spacing, the spiral cutter may be adaptable to vary the frequency of the spacing at discrete intervals to minimize delays during adjustment of the spacing interval. As with most linear fiber optics, as light is extracted from lengths of the fiber near the light source there may be less light available in subsequent lengths and this occurrence may be taken into consideration in the manufacturing process. In some embodiments, to achieve uniform lighting from the optical fiber, the frequency with which the illuminators occur may increase non-linearly in relation to the length of the conduit and the distance of the illuminators from the light source. In other words, the illuminators may be closer together as the distance from the light source increases. This may compensate for the attenuation of the light due to the loss experienced from the illuminators and the natural attenuation of the optic itself. The spacing may be made progressively closer or in groups of spacing in which the groups may progressively get closer but the distance between individual illuminators within each group may remain constant. In some embodiments, the illuminators may have progressive depths to make the optical fibers transmit light evenly along its length. When illuminators are made progressively deeper, the light pattern may be altered. The deeper the cuts, the wider the light pattern may become. When illuminators are made progressively closer, the light pattern may remain the same and the light output may be increased. In some embodiments, near uniformity of light output along the length of the conduit may be achieved in part due to the changes in the spacing of the illuminators and in part due to the uniformity of the size and angle of the illuminators. A mechanical cutter may be well adapted to provide such uniformity.

Figure 5:
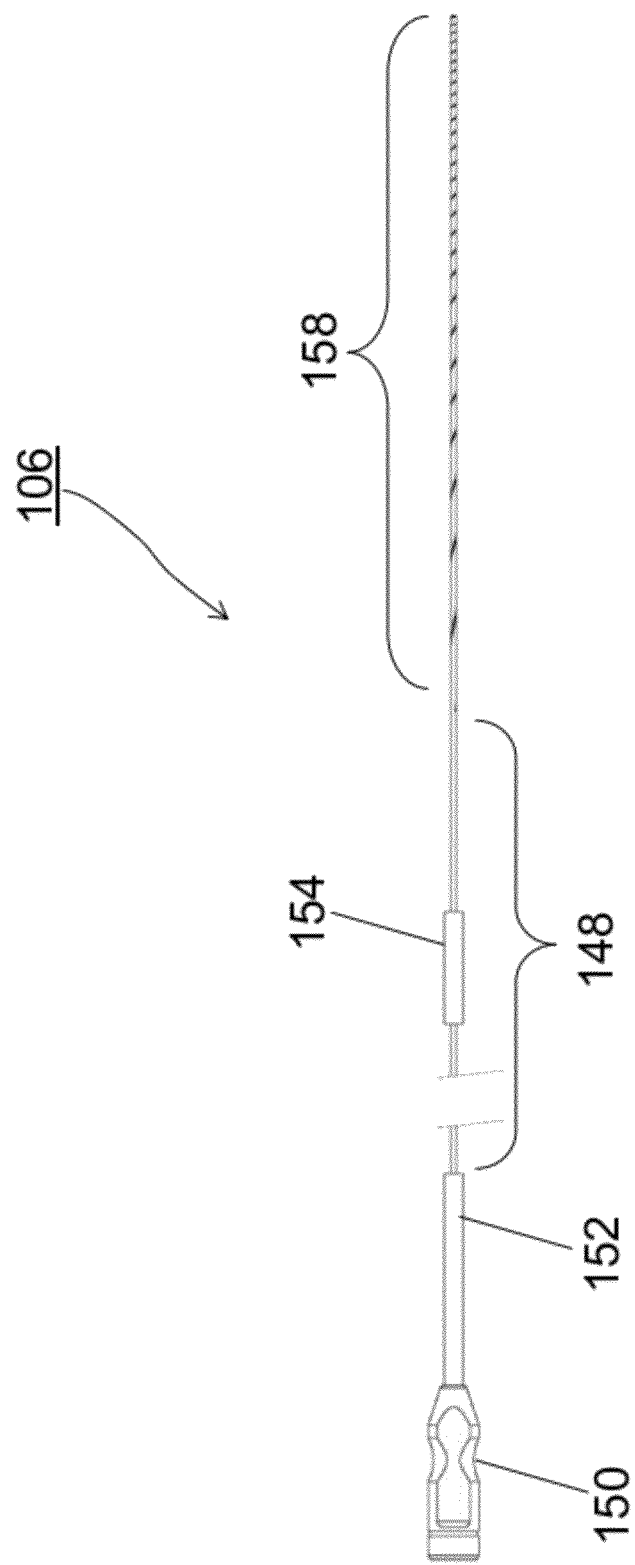
FIG. 5 shows an embodiment of an optical fiber of the present disclosure in an elongated stretched condition and being in a "temporary" shape.

As illustrated in FIG. 5, for example, the helical design produces cuts at a most proximal portion of the light-emitting portion that are spread farther apart than cuts at a most distal portion of the light-emitting portion. Typically, when an optical fiber is attached to a light source that is "on", the cuts at the proximal portion of the light-emitting portion will emit light that looks brighter than the cuts at the distal portion of the light-emitting portion.

It is desirable to provide shape memory to the light-emitting portion of an optical fiber of the present disclosure to create a nonlinear light-emitting portion of the optical fiber. In some embodiments, the shape memory is imparted to the light-emitting portion using conventional techniques known in the art. By way of a non-limiting example, a distal length of an optical fiber of the present disclosure may first be heat treated to provide stress relief, that is, to remove any shape memory from the optical fiber induced into the optical fiber during the manufacturing process. Heat treatment can also be used to induce a pre-set into the optical fiber. The distal length of the stress-relieved optical fiber may then be wound around a circular mandrel to provide the distal length with a desired shape. For example, in embodiments, the distal length of an optical fiber of the present disclosure may be preformed as a single loop or as multiple loops. Next, the mandrel with the coiled optical fiber can be subjected to heat treatment to induce the desired shape and then quenched to set the desired shape into the optical fiber. In an embodiment, the optical fiber may be heat treated using a water bath.

The nonlinear light-emitting portion can be any given length suitable for a given application. For example, a nonlinear light-emitting portion of an optical fiber of the present disclosure can have a length ranging from about 100 mm to about 300 mm. In an embodiment, a system of the present disclosure includes a balloon catheter including inflatable balloons that have a working length that is about 15 mm shorter than the length of the nonlinear light-emitting portion of the optical fiber. In an embodiment, a system of the present disclosure includes a balloon catheter including inflatable balloons that have a working length of about 85 mm and an optical fiber having a nonlinear light-emitting portion having a length of about 100 mm. In an embodiment, a system of the present disclosure includes a balloon catheter including inflatable balloons that have a working length of about 240 mm and an optical fiber having a nonlinear light-emitting portion having a length of about 255 mm. In an embodiment, a system of the present disclosure includes a balloon catheter including inflatable balloons that have a working length of about 285 mm and an optical fiber having a nonlinear light-emitting portion having a length of about 300 mm.

The illuminators may be made in optical fiber core alone before the cladding is added and/or the illuminators may be made in the cladding and the core after it has been surrounded by the cladding. In some embodiments, when the cladding is heated to tightly shrink around the core, the cladding may affect the uniformity of the illuminators in the core by either entering the notch or closing the cut thereby reducing the potential light deflecting properties of the illuminator.

The illuminators may be positioned to direct light across the greater diameter of an elliptical optical fiber core out and out through a region opposite from each of the respective illuminators. This may be accomplished by angling the notches and/or cuts to direct light from the light source through the optic core. The illuminators allow better control of escaping light by making the notches, which are positioned on one side of the optic to direct the light rather than allowing the cuts to reflect/refract light in various directions which reduces the contribution of light to a desired focusing effect.

In an embodiment, the total light output from a nonlinear light-emitting portion of the present disclosure having a length of about 100 mm is the same as a nonlinear light-emitting portion of the present disclosure having a length of about 300 mm. In an embodiment, the total light output required for the nonlinear light-emitting portion of an optical fiber of the present disclosure is about 20 $\mu W/cm^2$.

In some embodiments, where at least a portion of a length of the optical fiber has been modified by cutting the cladding material, the cuts may be made at a uniform depth of ⅛ inch into the cladding and core and at a 45 degree angle from the horizontal, i.e., the longitudinal axis of the optical fiber. This may appear to cause the light to exit perpendicular to the longitudinal axis of the optical fiber where the optical fiber core may have an acceptance angle of approximately 81 degrees to allow light to exit. The surface of the sides of the cut may be smooth rather than rough to ensure light is refracted uniformly. The cut may form a wedge which has a gap sufficient to prevent contact between the sides of the cut during normal use. Such contact may reduce the light reflecting and/or refracting properties. In some embodiments, the cuts may be less efficient than the notches in relying on TIR to force light out of core. A holder which may fix the optical fibers in desired alignment may also act as a holder and/or reflector. In some embodiments, when the optical fiber may be round in cross section and may be placed in a nonconforming holder such as a rectilinear "U" channel where an open space is created at the bottom of the "U", cuts may be made in the optical fibers that come in close proximity to the bottom of the "U" to maintain this configuration. In some embodiments where a conforming holder may be used, the cuts may close and alter the configuration such that efficiency of light extraction may be reduced. In some embodiments when using a conforming holder, illuminators may be made with notches sufficient to maintain an open space between the holder and notched surface.

In an embodiment, the nonlinear light-emitting portion includes circular steps that have been created or cut into an optical fiber to cause the light to disperse along each terminating face of each circular step of the optical fiber. In an embodiment, the nonlinear light-emitting portion is a portion that has been tapered along a length, and some of the cladding material has been removed. The tapering of the optical fiber can result in a radial dispersion of light from the optical fiber.

In an embodiment, the nonlinear light-emitting portion includes notches so as to cause the internal reflectance to be directed outwards at an angle from the notch in the optical fiber. The notch may function as an illuminator by maximizing the TIR effect of light within the core. This may be due to the core having a different index of refraction from the ambient air in the notch which may direct the light across the core and out the opposite side of the core. Different lighting effects may be achieved by replacing the ambient air with other gases or compounds. In some embodiments, cutting notches may include using a high speed drill motor with a cutting blade sufficient to make a notch in the optical fiber such that the surface created with the notch may be smooth enough to allow total internal reflection to occur. Alignment of illuminator or illuminators with respect to the holder may determine the directionality of the light output emitted from the optical system. The shape of the cut may effect the output beam pattern of the optical system. For example, the wider the cut, the wider the output beam pattern. Imperfections in the cut may direct some light into the notch. This light may reflects back through the core. In some embodiments, the notches may be created at about a 45 degree angle to the fiber. In some embodiments, the notches may be created at about a 30 degree angle, about a 62.5 degree angle or any angle less than about 45 degrees or greater than about 45 degrees as not all embodiments of the present disclosure are intended to be limited in this manner. Further, in some embodiments the angle of the notches may change depending on where the notch is located along the length of the fiber. For example, an optical fiber may be notched so that the angle of the notches which will be positioned at the ends of the balloon have a shallower angle than those to be positioned at middle of the balloon.

In some embodiments, the ends of individual optical fibers that make up an optical fiber bundle may be staggered to enable light to emit from the light source at various locations along the length of the fiber.

In some embodiments, the optical fiber may include an optical fiber core surrounded by cladding material and one or more illuminators. The illuminators may be of uniform size and shape positioned in a predetermined, spaced-apart relation, linearly, along a side of the optical fiber core. The optical fiber core may be received in a track and/or holder and/or reflector comprising a channel constructed with a reflective interior surface centered about the illuminators. The holder and/or reflector may be positioned adjacent to or in contact with the plurality of illuminators. A light source may be connected at one end of the optical fiber conduit in a conventional manner so as to cause a TIR effect. The end of the optical fiber conduit opposite the light source may include a reflective surface for reflecting back towards the light source any light remaining in the optical fiber conduit. For longer spans of optical conduit, the conduit may include a second light source.

The illuminators may include any non-uniformity, constructed into the optical fiber core during or after fabrication, that reflects or refracts light such as, for example bubbles, prisms, lenses or reflective material formed in the core during fabrication or after fabrication. Also, notches made from two cuts in the core to remove a wedge of material or singular cuts made in the core may function as the illuminators. Illuminators, such as notches or cuts may be made by using a mechanical cutter which may be capable of cutting the core uniformly and leaving a smooth, texture-free surface. A cutter suitable for this purpose may cut the core without tearing or burning the material. A cutter may have a circular disk shaped knife having a smooth, tooth-free blade that is freely rotatable about an axle located at the center of the disk. The blade may be angled at 45 degrees relative to the longitudinal axis of the core to cut a 90 degree notch wherein material having a crescent or triangular shape is removed from the core.

FIG. 5 shows an embodiment of an optical fiber 106 of the present disclosure fabricated from a flexible light transmitting material. The optical fiber 106 includes a hub 150 at a proximal end for attaching to a light source (either directly or indirectly, for example, through the use of an attachment system, see FIG. 1). The optical fiber 106 includes a linear elongated portion 148 for guiding light towards a nonlinear light-emitting portion, generally referred to as 158, which emits light from the outside of the fiber along its length. The nonlinear light-emitting portion 158 can be any length suitable for a given application. The distal tip of the optical fiber 106 may also emit light creating a small spotlight effect In an embodiment, the optical fiber 106 also includes a flexible strain relief 152 just to the right of the hub 150 and a depth stop 154. In an embodiment, the strain relief 152 prevents snapping of the optical fiber 106 at the hub 150 junction. In an embodiment, the strain relief 152 and the depth stop 154 are made from a flexible material. In an embodiment, the strain relief 152 and the depth stop 154 are made from Santoprene™, a thermoplastic rubber. FIG. 5 shows the optical fiber 106 in an elongated stretched condition and being in a "temporary" shape. In the temporary shape, the nonlinear light-emitting portion 158 is stretched and assumes a linear conformation in which the nonlinear light-emitting portion 158 of the optical fiber 106 can be advanced through the inner lumen of the elongated shaft of the balloon catheter 110.

FIG. 6, FIG. 7, FIG. 8 and FIG. 9 show various embodiments of nonlinear light-emitting portions 158a-d, respectively, of an optical fiber of the present disclosure, wherein a length of the optical fiber has been deformed and set (fixed) to form single or multiple curved, coiled and/or convoluted shapes, wherein the nonlinear light-emitting portions 158 is steerable through an inner lumen and/or an optical fiber conduit of the balloon catheter, wherein the nonlinear light-emitting portions 158 is flexible so as to move from a temporary substantially straight shape confined by the walls of the inner lumen and/or optical fiber conduit and return back to its original or permanent set shape when the nonlinear light-emitting portions 158 extends beyond the lumen and/or conduit confines and into an inner cavity of a balloon of the expandable member, and wherein the nonlinear light-emitting portions 158 is modified by removing a portion of a cladding material surrounding the nonlinear light-emitting portions 158 to disperse light energy along the length of the nonlinear light-emitting portions 158 so as to initiate hardening of the light-sensitive fluid within a balloon of the expandable member.

Figure 6:
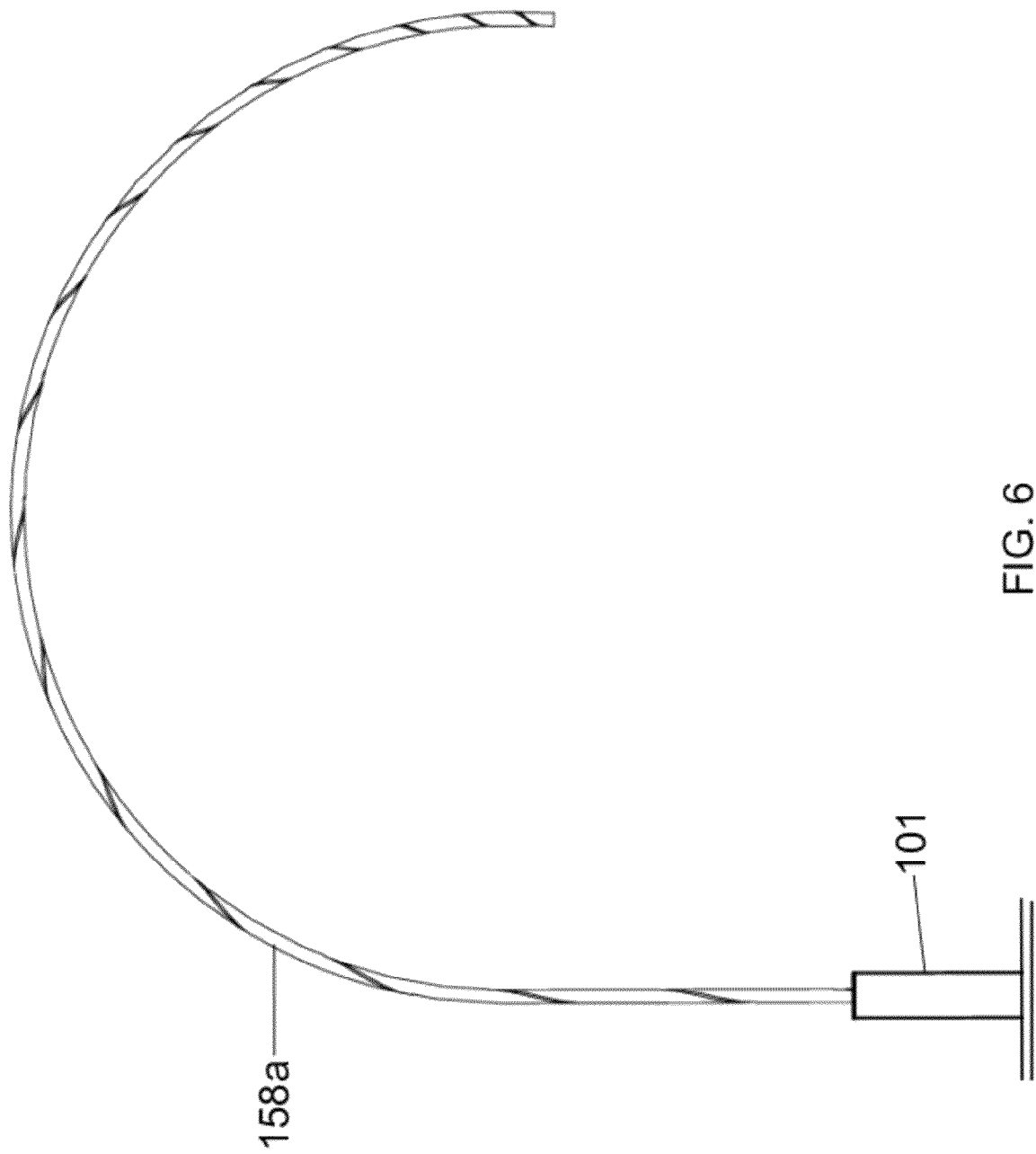
FIG. 6 shows an embodiment of a nonlinear light-emitting portion of an optical fiber of the present disclosure in a relaxed condition and being in an "original", "pre-shaped" or "permanent" shape.

FIG. 6 shows an embodiment of a nonlinear light-emitting portion 158a in a relaxed condition and being in an "original", "pre-shaped" or "permanent" shape. As illustrated in FIG. 6, in the relaxed condition, the nonlinear light-emitting portion 158a is in a curved conformation creating a "candy cane" or "J" shaped nonlinear light-emitting portion 158. When the curved nonlinear light-emitting portion 158a is stretched, the nonlinear light-emitting portion 158a elongates so that the entire length of the optical fiber 106 has a substantially straight longitudinal axis (see, for example, see FIG. 5). When elongated, the optical fiber 106 can traverse and advance through the inner lumen of the balloon catheter 110. Once the nonlinear light-emitting portion 158a has traversed the inner lumen of the balloon catheter 110, and enters the confines of the expandable member 103, the nonlinear light-emitting portion 158a will return back to its original, pre-shaped, permanent shape inside the expandable member 103. The return of the nonlinear light-emitting portion 158a from its stretched to its relaxed condition, is due to the memory imparted on the nonlinear light-emitting portion 158a. The nonlinear light-emitting portion 158a loops around and in close conformity to the inner wall of the inner cavity into which it is deployed (see, for example, see FIG. 12).

Figure 7:
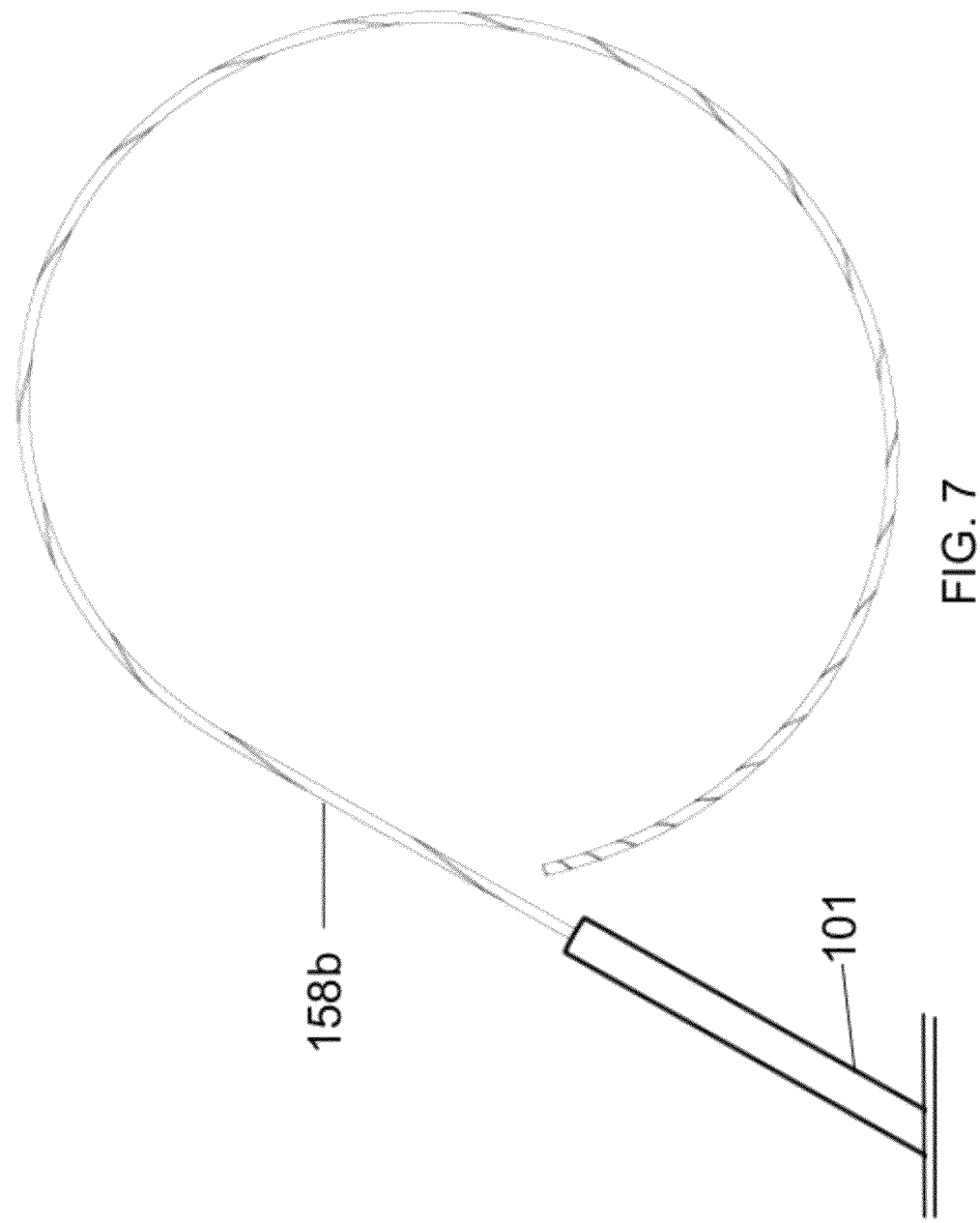
FIG. 7 shows an embodiment of a nonlinear light-emitting portion of an optical fiber of the present disclosure in a relaxed condition and being in an "original", "pre-shaped" or "permanent" shape.

FIG. 7 shows an embodiment of a nonlinear light-emitting portion 158b in a relaxed condition and being in an "original", "pre-shaped" or "permanent" shape. As illustrated in FIG. 7, in the relaxed condition, the nonlinear light-emitting portion 158b is in a curved conformation creating a "D" or "O" shaped nonlinear light-emitting portion 158b. When the curved nonlinear light-emitting portion 158b is stretched, the nonlinear light-emitting portion 158b elongates so that the entire length of the optical fiber 106 has a substantially straight longitudinal axis (see, for example, see FIG. 5). When elongated, the optical fiber 106 can traverse and advance through the inner lumen of the balloon catheter 110. Once the nonlinear light-emitting portion 158b has traversed the inner lumen of the balloon catheter 110, and enters the confines of the expandable member 103, the nonlinear light-emitting portion 158b will return back to its original, pre-shaped, permanent shape inside the expandable member 103. The return of the nonlinear light-emitting portion 158b from its stretched to its relaxed condition, is due to the memory imparted on the nonlinear light-emitting portion 158b. The nonlinear light-emitting portion 158b loops around and in close conformity to the inner wall of the inner cavity into which it is deployed.

Figure 8:
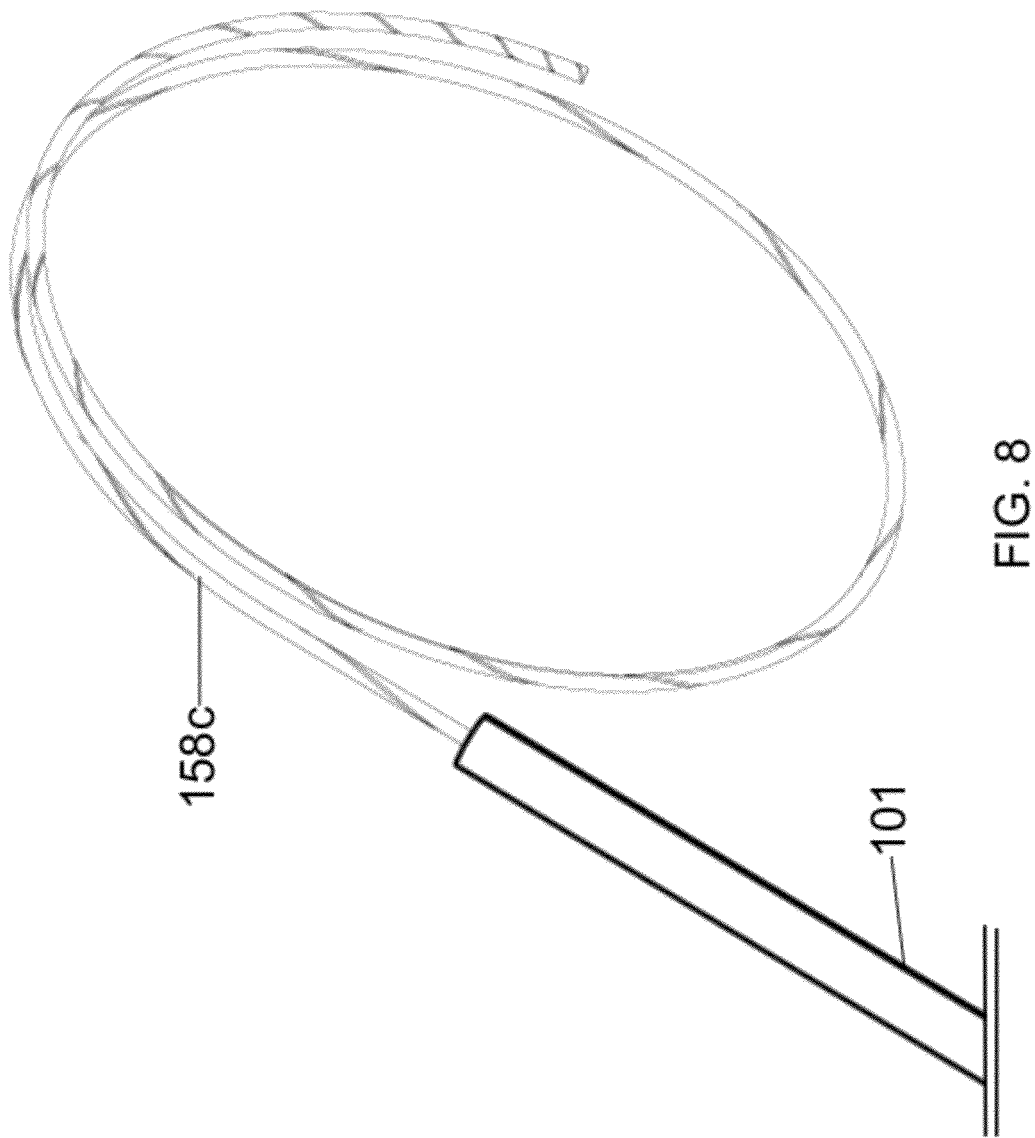
FIG. 8 shows an embodiment of a nonlinear light-emitting portion of an optical fiber of the present disclosure in a relaxed condition and being in an "original", "pre-shaped" or "permanent" shape.

FIG. 8 shows an embodiment of a nonlinear light-emitting portion 158c in a relaxed condition and being in an "original", "pre-shaped" or "permanent" shape. As illustrated in FIG. 8, in the relaxed condition, the nonlinear light-emitting portion 158c is in a curved conformation creating a "coiled" shaped nonlinear light-emitting portion 158c. When the coiled nonlinear light-emitting portion 158c is stretched, the nonlinear light-emitting portion 158c elongates so that the entire length of the optical fiber 106 has a substantially straight longitudinal axis (see, for example, see FIG. 5). When elongated, the optical fiber 106 can traverse the inner lumen of the balloon catheter 110. Once the nonlinear light-emitting portion 158c has traversed the inner lumen of the balloon catheter 110, and enters the confines of the expandable member 103, the nonlinear light-emitting portion 158c will return back to its original, pre-shaped, permanent shape inside the expandable member 103. The return of the nonlinear light-emitting portion 158c from its stretched to its relaxed condition, is due to the memory imparted on the nonlinear light-emitting portion 158c. The nonlinear light-emitting portion 158c loops around and in close conformity to the inner wall of the inner cavity into which it is deployed.

Figure 9:
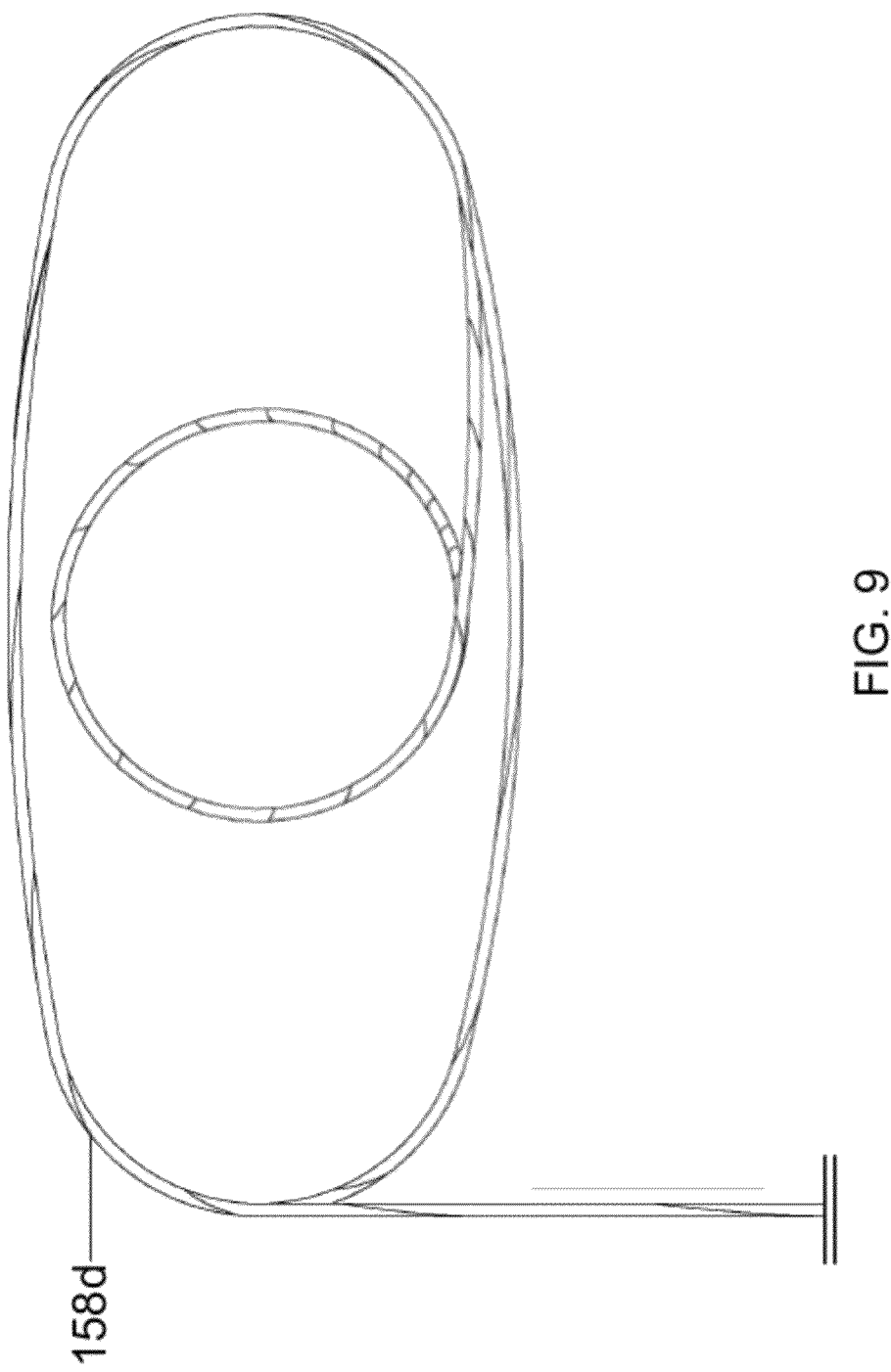
FIG. 9 shows an embodiment of a nonlinear light-emitting portion of an optical fiber of the present disclosure in a relaxed condition and being in an "original", "pre-shaped" or "permanent" shape.

FIG. 9 shows an embodiment of a nonlinear light-emitting portion 158d in a relaxed condition and being in an "original", "pre-shaped" or "permanent" shape. As illustrated in FIG. 9, in the relaxed condition, the nonlinear light-emitting portion 158d is in a curved conformation create a "coiled convoluted" shaped light-emitting portion 158d, having numerous coils or folds. When the convoluted nonlinear light-emitting portion 158d is stretched, the nonlinear light-emitting portion 158d elongates so that the entire length of the optical fiber 106 has a substantially straight longitudinal axis (see, for example, see FIG. 5). When elongated, the optical fiber 106 can traverse the inner lumen of the balloon catheter 110. Once the nonlinear light-emitting portion 158d has traversed the inner lumen of the balloon catheter 110, and enters the confines of the expandable member 103, the nonlinear light-emitting portion 158d will return back to its original, pre-shaped, permanent shape inside the expandable member 103. The return of the nonlinear light-emitting portion 158d from its stretched to its relaxed condition, is due to the memory imparted on the nonlinear light-emitting portion 158d. The nonlinear light-emitting portion 158d loops around and in close conformity to the inner wall of the inner cavity into which it is deployed (see, for example, see FIG. 13).

In an embodiment, an optical fiber of the present disclosure is manufactured from a Lumenyte STA-FLEX® "SEL" END LIGHT OPTICAL FIBER, available from Lumenyte International Corporation of Foothill Ranch, Calif., can be employed. These optical fibers may each consist of a light transmitting solid large core, a Teflon® clad and a black bondable outer jacket. The optical fiber may transmit light from a light source to the distal tip for use as a point source. The optical fiber may have a wide 80 degree acceptance angle and 80 degree beam spread, allowing the light to be viewed from more oblique angles. The light transmitting core may be solid, may have no light diminishing packing fraction losses and may be easily spliced. The jacket may be bondable. Custom jackets may be available for more flexibility and color options. The optical fiber can each have a transmission loss (attenuation) of less than approximately 1.5% per foot, a bend radius (minimum) of approximately 6 times the fiber's diameter, temperature stability of up to approximately 90° C. (194° F.), spectral transmission range of approximately 350-800 nm, an acceptance angle of approximately 80°, a refractive index core of approximately 1.48 or greater, cladding of approximately 1.34 or less and a numerical aperture of approximately 0.63. The length of the optical fiber can be approximately 100 continuous feet. Splicing may be achieved in the field using a splice kit, such as the Lumenyte Splice Kit, and carefully following the instructions. Factory splicing may be an option. An optic cutter, such as Lumenyte's Optic Cutter, may be advised for straight, clean, 90° fiber cuts. These fibers may be installed by removing approximately 4 inches (10 cm) of the outer jacket (not the fluoropolymer cladding) before inserting fiber into the light source. An end of the fiber may be near, but not touching the illuminator (light source) glass to assist in achieving maximum brightness.

In an embodiment, an optical fiber of the present disclosure is manufactured from a ESKA™ High-performance Plastic Optical Fiber: SK-10 and SK-60 and/or ESKA™ Plastic Fiber Optic & Cable Wiring, manufactured by Mitsubishi Rayon Co., Ltd., which are all available from Mitsubishi International Corporation of New York, N.Y. These optical fibers may each consist of a light transmitting PMMA (polymethylmethacrylate) core and a fluorinated polymer as the cladding. It should be appreciated that the above-described characteristics and properties of the optical fibers are exemplary and not all embodiments of the present invention are intended to be limited in these respects.

In some embodiments, optical elements may be oriented in alignment with the notches, cuts or openings in the nonlinear light-emitting portion of an optical fiber of the present disclosure to adjust the light output. Such optical elements may include lenses, prisms, filters, spliters, diffusers and/or holographic films. The light source, and more specifically, the optical fibers may have some or all of the properties and features listed in U.S. Pat. No. 6,289,150, which is hereby incorporated by reference in its entirety, as not all embodiments of the present invention are intended to be limited in these respects.

One or more optical elements, such as diffusers, polarizers, magnifying lenses, prisms, holograms or any other element capable of modifying the direction, quantity or quality of the illumination, individually or in combination can also be added and aligned with the core-clad, notches and track or holder and/or reflector. The optical elements may be formed as separate components or formed integrally with the core, cladding and/or a jacketing material or in any combination of separate and integrally formed components. Optical elements formed integrally in the core and cladding of various shapes may create a lens and thereby affects the directionality of light from the finished product. Different optical fiber shapes may create different output beam patterns. In some embodiments, a round fiber optic may create a wider beam spread of light. In some embodiments, a wedge shaped optic may produce a collimated light beam spread. This beam spread may be due to what is believed to be a lensing effect. In some embodiments, the depth of the cut may at least intersect the focal point of the lens formed by the curvature of the optical fiber core where the light exits the core.

The optical fiber core may have any shape and the shape of the core may effect the diffusion of light. In some embodiments, the optical fiber core may be cylindrically shaped when viewed in cross-section and may form a lens that diffuses the light over a wide field of illumination. In some embodiments, the optical fiber core may have an oval or elliptical shape when viewed in cross-section and may form a lens that increases the intensity of the light within a narrower field of illumination. In some embodiments, the optical fiber core may have a wedge shape when viewed in a cross-section and may forms a lens. It will be appreciated that other shapes may be used because of their desired optical characteristics to also act as optical elements, as not all embodiments of the present invention are intended to be limited in this respect.

Alternative optical elements may also assist in achieving various lighting effects by including a separate optical element in alignment with the holder and/or reflector and the arc formed by the notch on the opposite side of the optic from the optical element. The lens optic, notch and holder and/or reflector may be aligned to direct light out of the optic and into the lens. The optical element may also be formed integrally in the jacketing material. The jacket thickness may be adjusted to achieve a desired lighting effect. Alternatively, cylindrically shaped diffusers may be included and aligned to generate other desired lighting effects. In some embodiments, a first diffuser may lower the intensity of light passing through an optical fiber and a second diffuser may increase the intensity of light passing through it. The two diffusers as thus described, may modify the intensity of light as it transmits and diverges away from the optical fiber.

In order to best make use of this kind of application specific optical lighting, it may be advisable to control the alignment of the illuminators, holder and/or reflectors and optical elements. In some embodiments, the alignment of these elements may be centered about a diameter of the fiber optic core (e.g., the diameter from and perpendicular to the center of the holder and/or reflector). It may be desirable to maintain control of this alignment along the entire length of the optical fiber conduit.

An optical fiber of the present disclosure can be made from any material, such as glass, silicon, silica glass, quartz, sapphire, plastic, combinations of materials, or any other material, and may have any diameter. In an embodiment, the optical fiber is made from silica glass and may have wide-angle light dispersion of about 88 degrees. In an embodiment, the optical fiber is made from a plastic material. In an embodiment, the optical fiber is steerable to enable the optical fiber to be maneuvered through the balloon catheter to the expandable member. The optical fiber is flexible and malleable to be maneuverable through a device of the present disclosure. In an embodiment, the optical fiber is shapeable and/or bendable in all directions.

The core of the optical fiber may have any shape and the shape of the core may effect the diffusion of light. In some embodiments, the core of the optical fiber may be cylindrically shaped when viewed in cross-section and may form a lens that diffuses the light over a wide field of illumination. In some embodiments, the core of the optical fiber may have an oval or elliptical shape when viewed in cross-section and may form a lens that increases the intensity of the light within a narrower field of illumination. In some embodiments, the core of the optical fiber may have a wedge shape when viewed in a cross-section and may forms a lens. It will be appreciated that other shapes may be used because of their desired optical characteristics to also act as optical elements, as not all embodiments of the present invention are intended to be limited in this respect.

In an embodiment, the optical fiber emits light radially in a uniform manner along a length of the nonlinear light-emitting portion of the optical fiber in addition to or instead of emitting light from its terminal end/tip. In an embodiment, the manner in which the light-sensitive fluid is expected to be illuminated may be modeled in accordance with Snell's law, taking into account the shape of the distal portion of the optical fiber, angles of incidence of light from the optical fiber, refractive indexes of the inflation fluid, balloon walls, and light-sensitive fluid. In an embodiment, the optical fiber is configured to exude light along at least a portion of the pre-shaped nonlinear light-emitting portion of the optical fiber. In another embodiment, the optical fiber is configured to exude light along the entire length of the pre-shaped nonlinear light-emitting portion of the optical fiber. To that end, all or part of the cladding material along the pre-shaped nonlinear light-emitting portion of the optical fiber may be removed. It should be noted that the term "removing cladding" includes taking away the cladding material entirely to expose the optical fiber as well as reducing the thickness of the cladding material. In addition, the term "removing cladding" includes forming an opening, such as a cut, a notch, or a hole, through the cladding material. In an embodiment, removing all or part of the cladding material may alter the propagation of light along the optical fiber. In another embodiment, removing all or part of the cladding material may alter the direction and angle of incidence of light exuded from the optical fiber. In yet another embodiment, removing all or part of the cladding material along the pre-shaped nonlinear light-emitting portion of the optical fiber may alter the intensity of light exuded from the pre-shaped nonlinear light-emitting portion of the optical fiber. In an embodiments, removing all or part of the cladding material along the pre-shaped nonlinear light-emitting portion of the optical fiber may alter the amount of light exuded from the pre-shaped nonlinear light-emitting portion of the optical fiber. In an embodiments, removing all or part of the cladding material along the pre-shaped nonlinear light-emitting portion of the optical fiber may alter the incidence of light exuded from the pre-shaped nonlinear light-emitting portion of the optical fiber. In an embodiments, removing all or part of the cladding material along the pre-shaped nonlinear light-emitting portion of the optical fiber may alter the uniformity and/or distribution of light exuded from the pre-shaped nonlinear light-emitting portion of the optical fiber.

The nonlinear light-emitting portion of an optical fiber of the present disclosure is straight during advancement through the elongated shaft of the balloon catheter into the expandable member. However, once inside the expandable member, because the nonlinear light-emitting portion of the optical fiber is pre-shaped and imparted with memory, the nonlinear light-emitting portion of the optical fiber can return to a relaxed condition in which the nonlinear light-emitting portion of the optical fiber assumes a curved conformation. In an embodiment, the nonlinear light-emitting portion of the optical fiber curves around the outer wall of the inner balloon. In an embodiment, the nonlinear light-emitting portion of the optical fiber curves around the outer wall of the inner balloon in a separate optical fiber conduit. In an embodiment, the nonlinear light-emitting portion of the optical fiber curves inside the inner wall of the inner balloon. In an embodiment, the nonlinear light-emitting portion of the optical curves inside the inner wall of the inner balloon in a separate optical fiber conduit. In an embodiment, the nonlinear light-emitting portion of the optical fiber curves, loops and/or coils inside the cavity of the inner balloon. Once the optical fiber is deployed in the expandable member, the light source may be activated so the light from the optical fiber illuminates a light-sensitive fluid contained in the inner balloon, causing the light sensitive fluid to cure. Because of the shape of the nonlinear light-emitting portion, and the removal of at least a portion of cladding material along the length of the nonlinear light-emitting portion, the optical fiber can exude light radially in a uniform manner, so the light is evenly dispersed. In an embodiment, the light is evenly dispersed from outside the inner balloon towards the inside of the inner balloon to cure the light-sensitive fluid contained therein. In an embodiment, the light is evenly dispersed from inside the inner balloon toward the outside of the inner balloon to cure the light-sensitive fluid contained therein. Due to its shape, the nonlinear light-emitting portion illuminates the light-sensitive fluid in a substantially circumferential manner. Also, because the nonlinear light-emitting portion is flexible and has shape memory it can continue to stay in conformance with the walls of the balloon even if the shape or size of the balloon changes during the curing step. Moreover, due to its shape, the nonlinear light-emitting portion may also serve to move the outer balloon from a deflated state to an inflated state or to support the outer balloon in an inflated state.

In some embodiments, the intensity of light may be sufficient enough to reach the distal end of the expandable member if the optical fiber is held in close proximity to or contacting/abutting the expandable member. By knowing the energy required to cure the light-sensitive fluid and calculating the distance from the optical fiber to the most distal aspect of the expandable member, the inverse square law may be used to calculate how much energy will dissipate over the distance and therefore whether the optical fiber can be abutted to the expandable member or need be placed within the expandable member so that it is closer to the light-sensitive fluid. Not only is the distance from the optical fiber to the light-sensitive fluid reduced by placing the optical fiber inside the expandable member, but the overall necessary intensity of light may be reduced.

Figure 10:
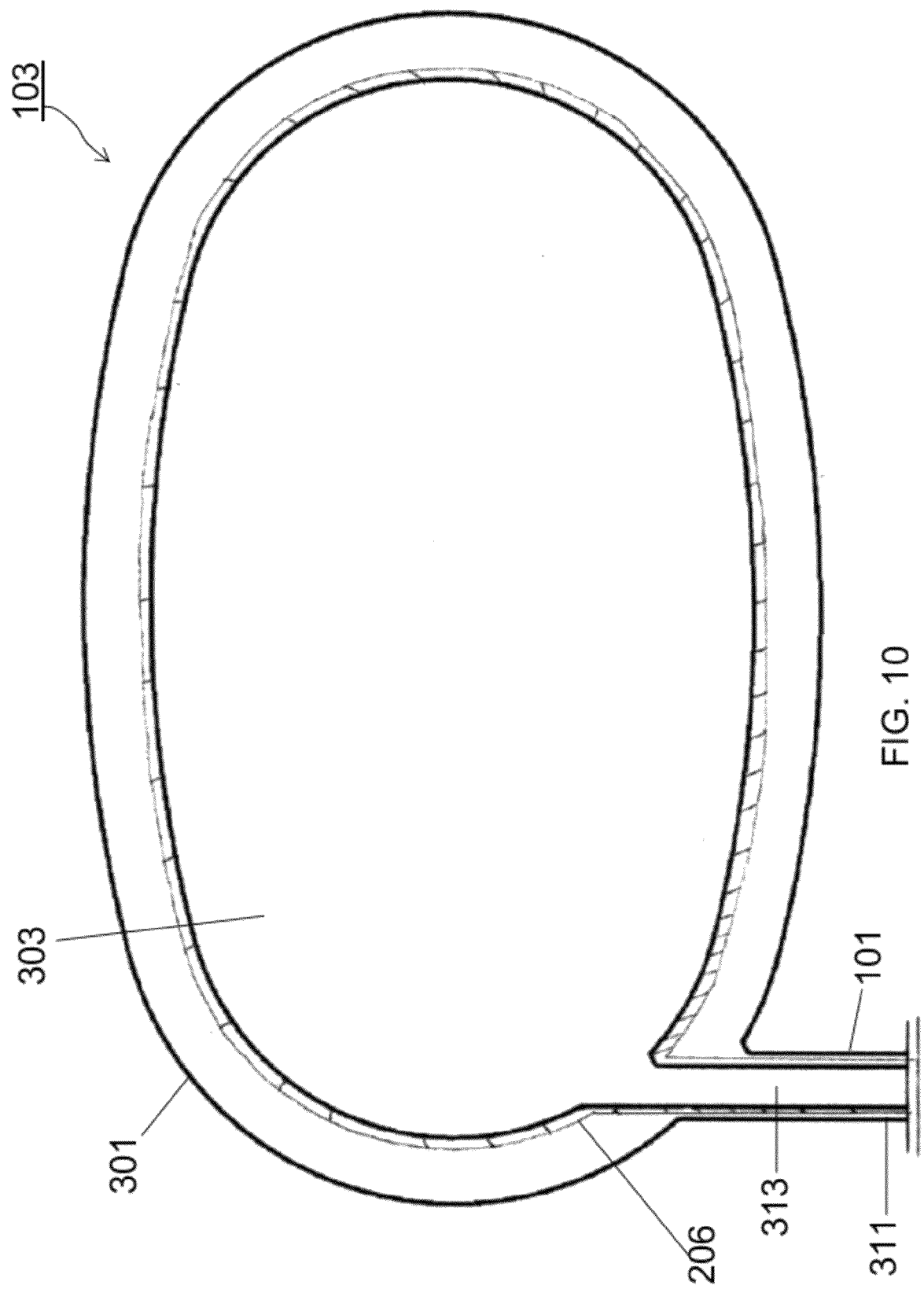
FIG. 10 shows a close-up view of an embodiment of a distal end of a balloon catheter of the present disclosure.

FIG. 10 shows a close-up view of an embodiment of a distal end of a balloon catheter of the present disclosure. The distal end of the balloon catheter includes expandable member 103, which comprises an outer inflatable balloon 301 and an inner inflatable balloon 303. The balloon catheter includes an elongated shaft having a first inner lumen 311 in fluid communication with the outer expandable balloon 301, a second inner lumen 313 in fluid communication with the inner expandable balloon 303. In addition, a separate optical fiber conduit 206 is incorporated within the elongated shaft of the balloon catheter and encircles the outer surface of the inner expandable balloon 303 to separate the optical fiber from other components of the balloon catheter, allowing the optical fiber to be removed from the balloon catheter after curing the light-sensitive fluid. In an embodiment, the optical fiber conduit 206 is fabricated from a thin walled PET tube.

Figure 11:
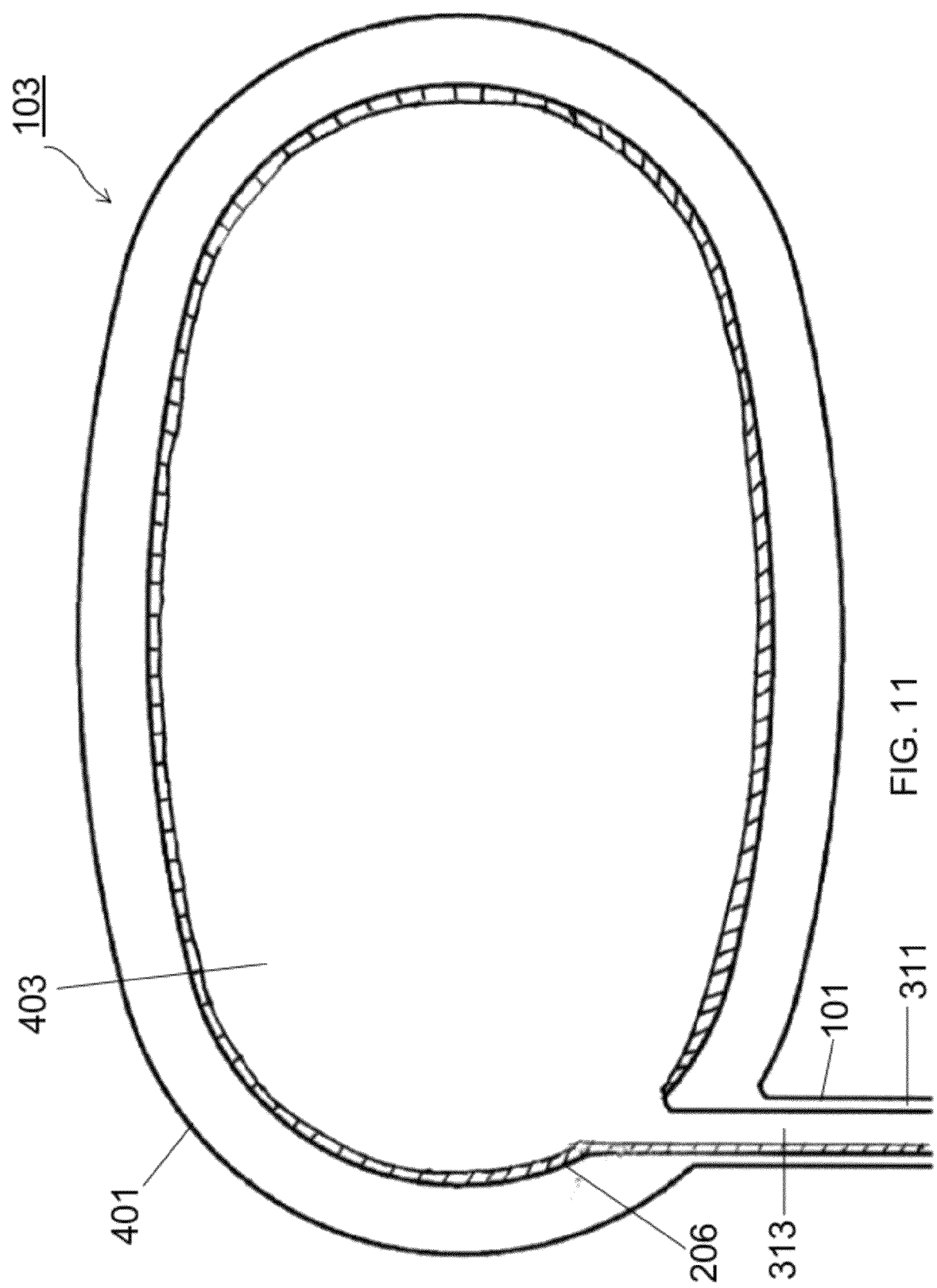
FIG. 11 shows a close-up view of an embodiment of a distal end of a balloon catheter of the present disclosure.

FIG. 11 shows a close-up view of an embodiment of a distal end of a balloon catheter of the present disclosure. The distal end of the balloon catheter includes expandable member 103, which comprises an outer expandable balloon 401 and an inner expandable balloon 403. The balloon catheter includes an elongated shaft having a first inner lumen 411 in fluid communication with the outer expandable balloon 401, a second inner lumen 413 in fluid communication with the inner expandable balloon 403. In addition, a separate optical fiber conduit 206 is incorporated within the elongated shaft of the balloon catheter and encircles the inner surface of the inner expandable balloon 403 to separate the optical fiber from other components of the balloon catheter, allowing the optical fiber to be removed from the balloon catheter after curing the light-sensitive fluid. In an embodiment, the optical fiber conduit 206 is fabricated from a thin walled PET tube.

Figure 12:
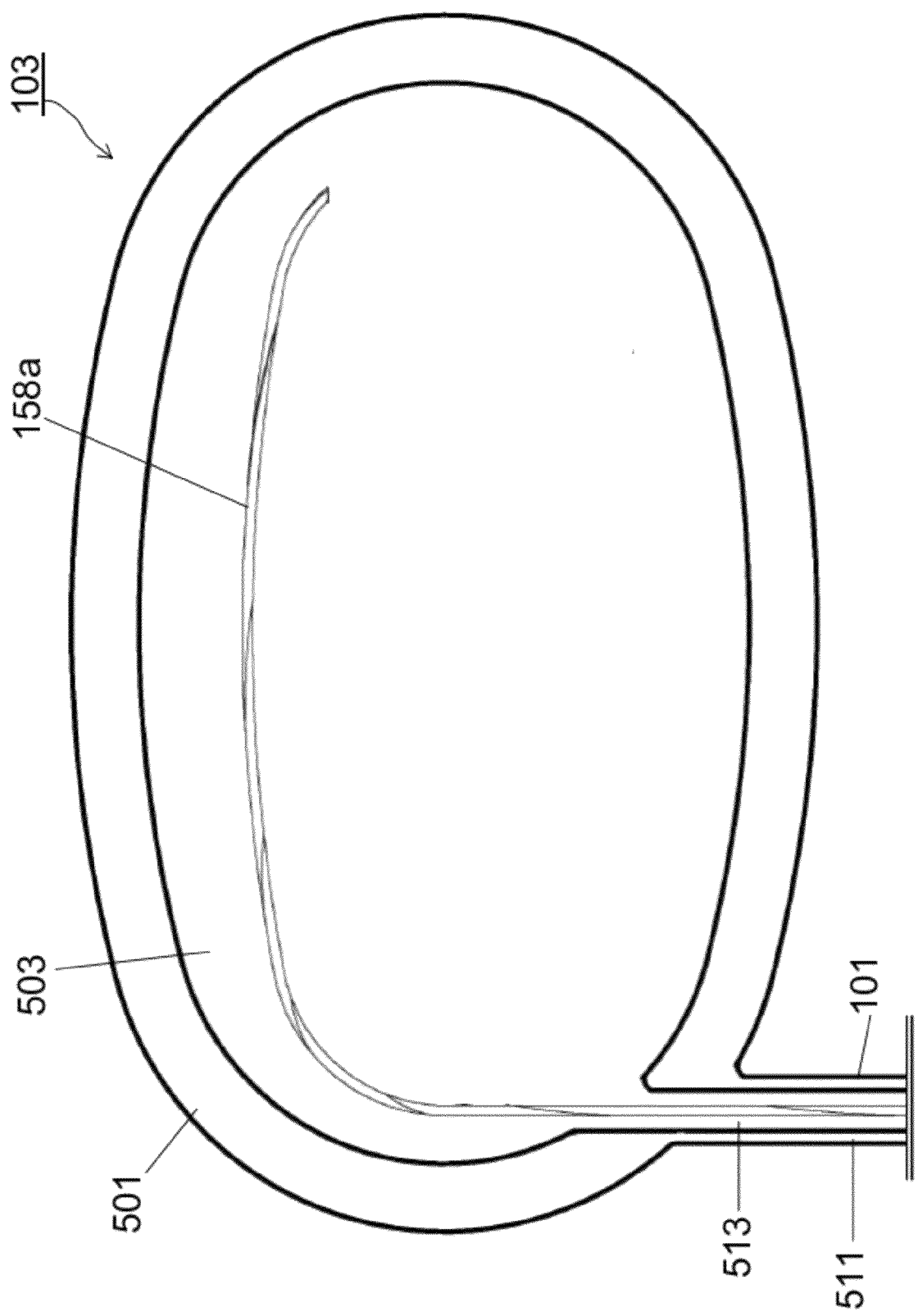
FIG. 12 shows a close-up view of an embodiment of a distal end of a balloon catheter of the present disclosure.

FIG. 12 shows a close-up view of an embodiment of a distal end of a balloon catheter of the present disclosure. The distal end of the balloon catheter includes expandable member 103, which comprises an outer expandable balloon 501 and an inner expandable balloon 503. The balloon catheter includes an elongated shaft having a first inner lumen 511 in fluid communication with the outer expandable balloon 501, a second inner lumen 513 in fluid communication with the inner expandable balloon 503. The nonlinear light-emitting portion 158a of the optical fiber returns from the stretched condition, in which the nonlinear light-emitting portion 158a has a linear conformation for advancing through the second inner lumen 513 of the elongated shaft 110 of the balloon catheter, to the relaxed condition, in which the nonlinear light-emitting portion 158a assumes the curved conformation, when released into the inner expandable balloon 503.

Figure 13:
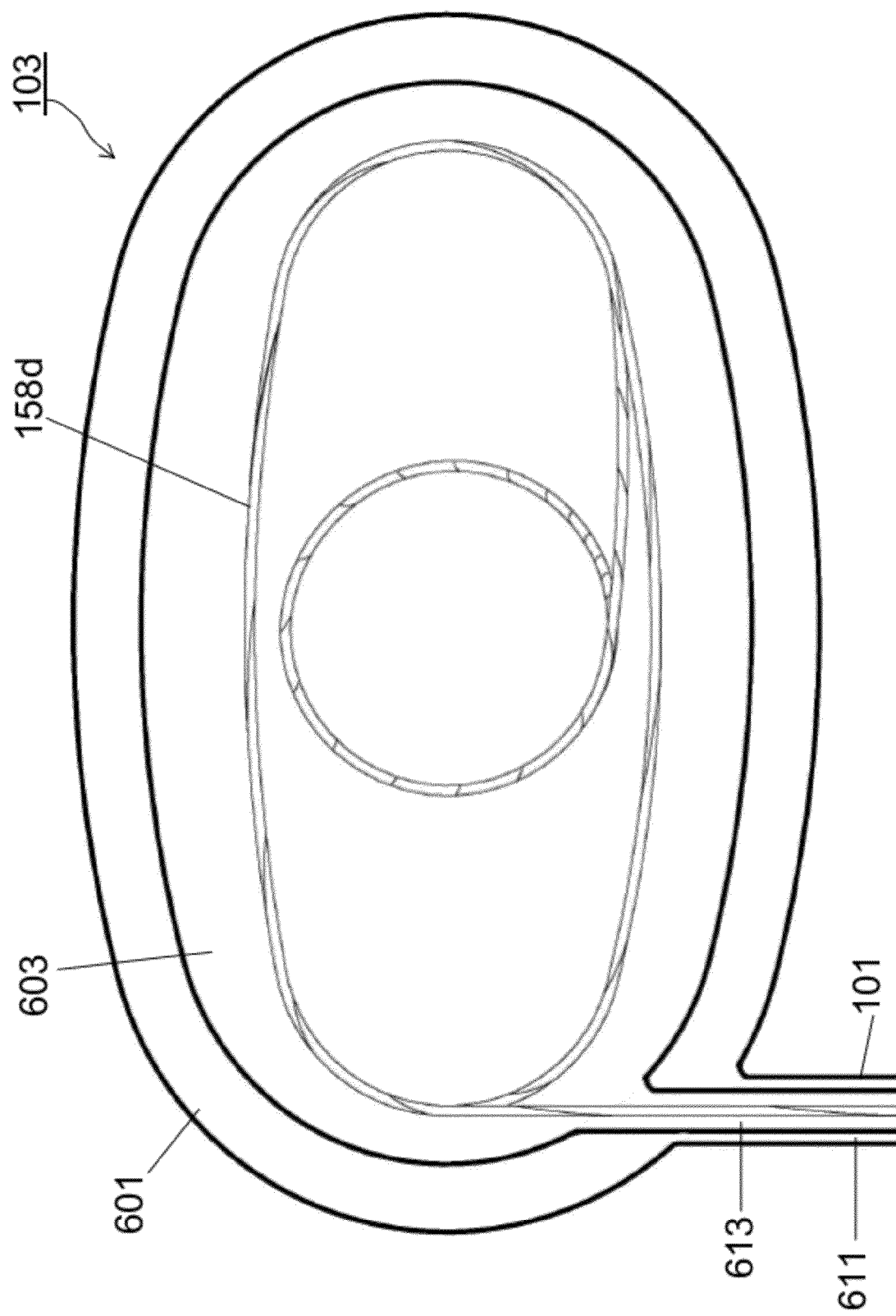
FIG. 13 shows a close-up view of an embodiment of a distal end of a balloon catheter of the present disclosure.

FIG. 13 shows a close-up view of an embodiment of a distal end of a balloon catheter of the present disclosure. The distal end of the balloon catheter includes expandable member 103, which comprises an outer expandable balloon 601 and an inner expandable balloon 603. The balloon catheter includes an elongated shaft having a first inner lumen 611 in fluid communication with the outer expandable balloon 601, a second inner lumen 613 in fluid communication with the inner expandable balloon 603. The nonlinear light-emitting portion 158d of the optical fiber returns from the stretched condition, in which the nonlinear light-emitting portion 158d has a linear conformation for advancing through the second inner lumen 613 of the elongated shaft 110 of the balloon catheter, to the relaxed condition, in which the nonlinear light-emitting portion 158d assumes the coiled convoluted conformation, when released into the inner expandable balloon 603.

FIGS. 14A-14E illustrate an embodiment of the method steps for repairing a vertebral compression fracture using components of the present disclosure. In an embodiment, the method relieves the pain of broken vertebrae and restores height to a hunched-over patient. To that end, a minimally invasive incision (not shown) may be made through the skin of the patient's body near the spine and a cannula (not shown) may be inserted percutaneously into a cancellous bone region 701 of a collapsed or fractured vertebra 703, for example via the left or right pedicle of the vertebra. The cannula may be any type and size of hollow cannula, preferably having a sharp end.

Figure 14A:
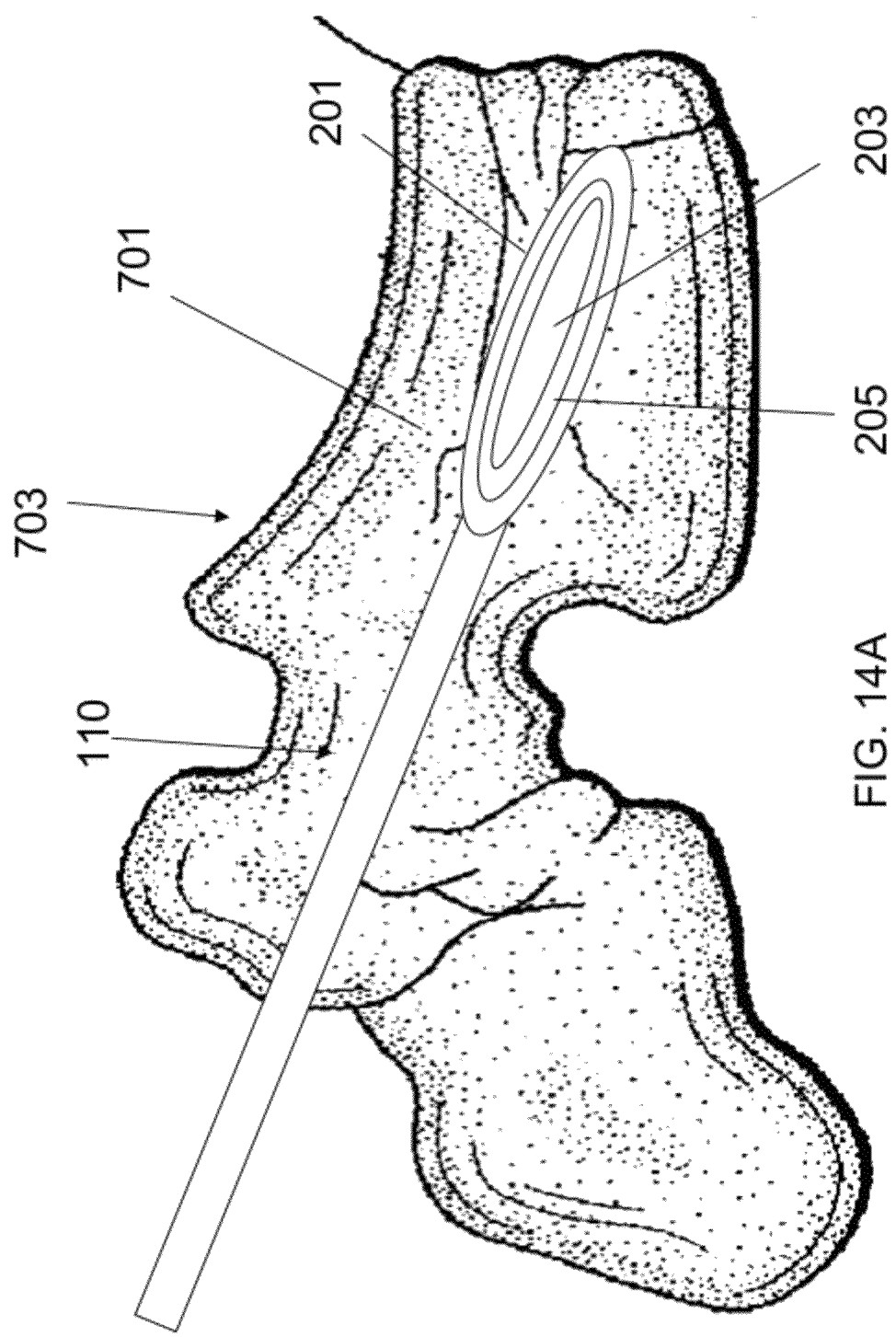

Next, a balloon catheter 110 of the present disclosure may be advanced through the cannula to position the expandable member 103, with the plurality of balloons 201, 203, 205 in an unexpanded, deflated state, in the cancellous bone region 701 of the collapsed or fractured vertebra 703, as illustrated in FIG. 14A. In an embodiment, the expandable member 103 is delivered to the spine by the flexible balloon catheter 110 from the posterior aspect of a patient. During insertion of the expandable member 103 into the collapsed or fractured vertebra 703, the location of the expandable member 103 may be monitored using visualization equipment such as real-time X-Ray, CT scanning equipment, MRI, or any other commonly used monitoring equipment. Once the expandable member 103 is positioned within the collapsed or fractured vertebra 703, an inflation fluid 705 may be injected into the outmost inner cavity 219 to move the outer balloon 201 from a deflated state to an inflated state, as shown in FIG. 14B. In an embodiment, the inflation fluid 705 is water or saline. In an embodiment, the inflation fluid 705 is air. As the outer balloon 201 moves from a deflated state to an inflated state, the outer balloon 201 expands the collapsed or fractured vertebra 703 so as to achieve controlled distraction and height restoration. An optical fiber 106 of the present disclosure may be inserted into the expandable member 103 before or after the outmost inner cavity is filled with the inflation fluid 705.

Additionally or alternatively, the balloons may be moved from a deflated state to an inflated state by inserting the pre-shaped optical fiber 106 into one or more inner cavities within the balloon. To move a balloon from an inflated state to a deflated state the inflation fluid, and, if applicable, the optical fiber, may be withdrawn from one or more inner cavities within the balloon.

In an embodiment, the balloons of the expandable member 103 may be configured so that in operation the balloons can only expand in a vertical direction to affect the height of the vertebra, but not in a horizontal direction to avoid exerting undue pressure on the side walls of the vertebra. In an embodiment, to achieve this goal, the side walls of the balloons may be reinforced or made of a stronger material than the top and bottom sides of the balloons.

Once the collapsed or fractured vertebra 703 is expanded to a desired height and distraction, the inmost inner balloon 203 may be moved from a deflated state to an inflated state by infusing a light-sensitive fluid 707 into the inmost inner cavity 223. It should be noted that it may be desirable, in an embodiment, to distract the collapsed or fractured vertebra 703 to a height slightly greater than the desired height to allow for subsequent compression and compaction of the space created by the outer balloon 201 in the cancellous bone region 701 once the outer balloon 201 is deflated at the end of the procedure. The final height of the vertebra may be adjusted using the intermediate inner balloon 205 and/or the outer balloon 201. Because the outer balloon 201 remains in the inflated state to maintain the distraction of the vertebra, the inmost inner balloon 203 is expanded with minimal backpressure, and thus a low pressure system may be used to infuse the light-sensitive fluid 707 into the inmost inner cavity 223 to inflate the inmost inner balloon 203.

Figure 14C:
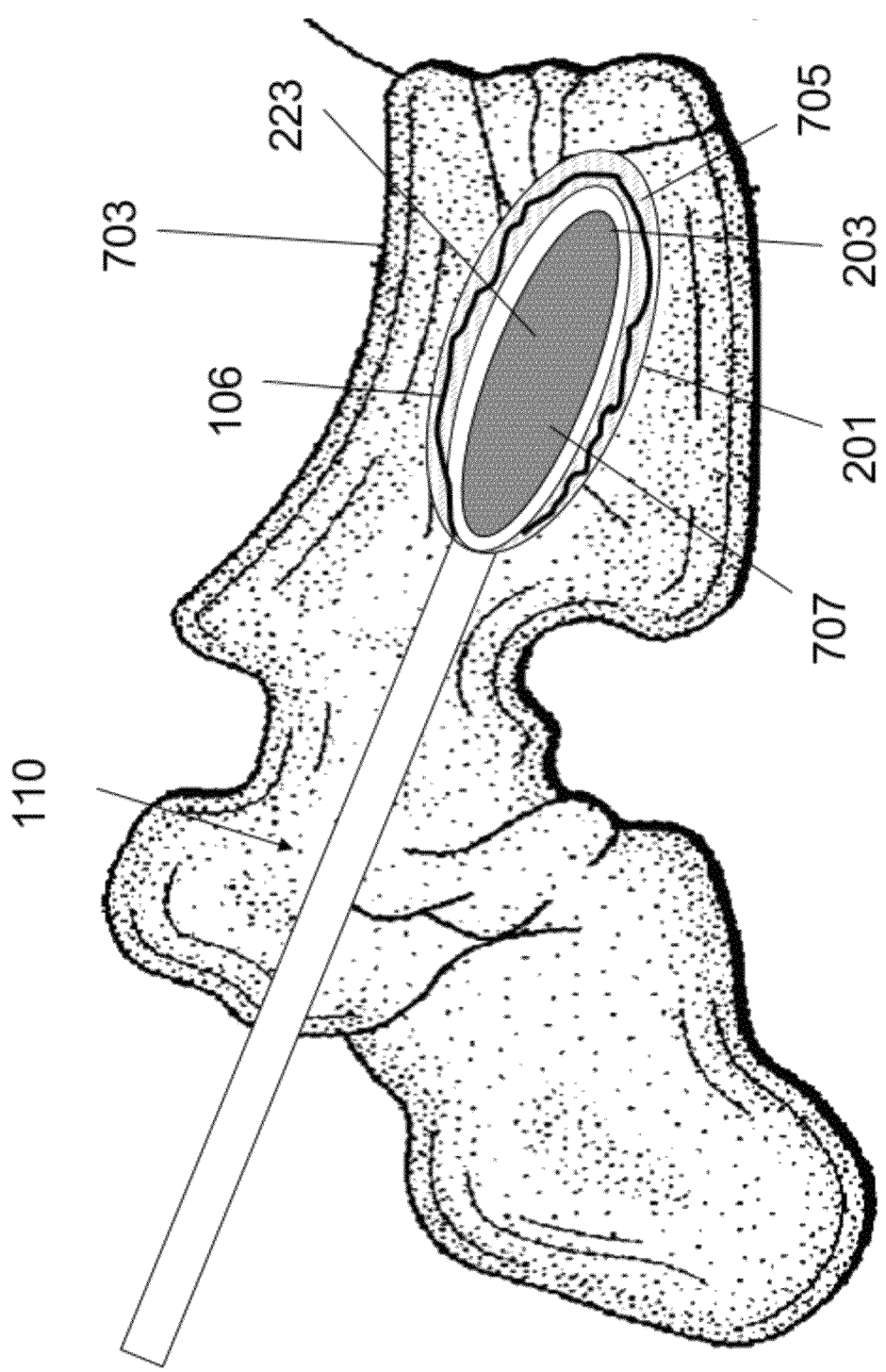

The light-sensitive fluid 707 in the inmost inner cavity 223 may be hardened by inserting the pre-shaped optical fiber 106 into the outmost inner cavity 219, as shown in FIG. 14C, or the intermediate inner cavity 221, or the inmost inner cavity 223 and activating the optical fiber 106 to illuminate the light-sensitive fluid 707 in the inmost inner cavity 223. As noted above, because the optical fiber 106 is pre-shaped, it can loop in conformance with the inmost inner cavity 219 and, thus provide uniform illumination of the light-sensitive fluid 707 contained in the inmost inner cavity 223 to cure the light-sensitive fluid 707 from outside of the inmost inner 223 cavity into the inmost inner cavity 223. During the curing step, the outer balloon 201 may remain inflated with the inflation fluid 705 to maintain the desired height of the collapsed or fractured vertebra 703. In an embodiment, the inflation fluid 705 inside the outmost inner cavity 219 acts as a cooling medium and as a barrier to any heat transfer between curing light-sensitive fluid 707 and vertebral tissue 701 and surrounding spinal nerves. In an embodiment, the inflation fluid 705 may be circulated during the curing step to ensure that the inflation fluid 705 is maintained at a substantially constant temperature throughout the procedure. In an embodiment, a thermocouple may be used to monitor the temperature of the inflation fluid.

Figure 14D:
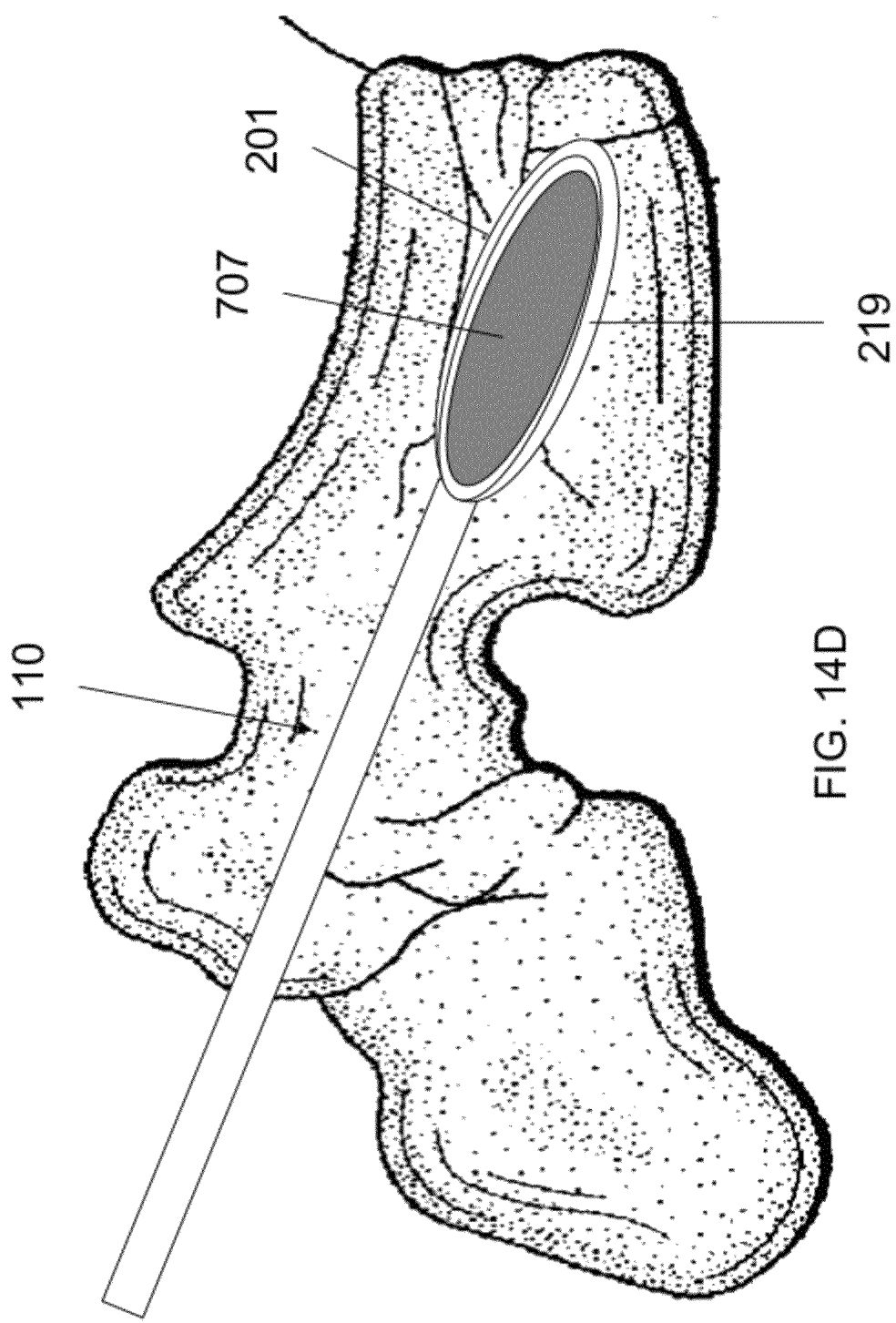
Figure 14E:
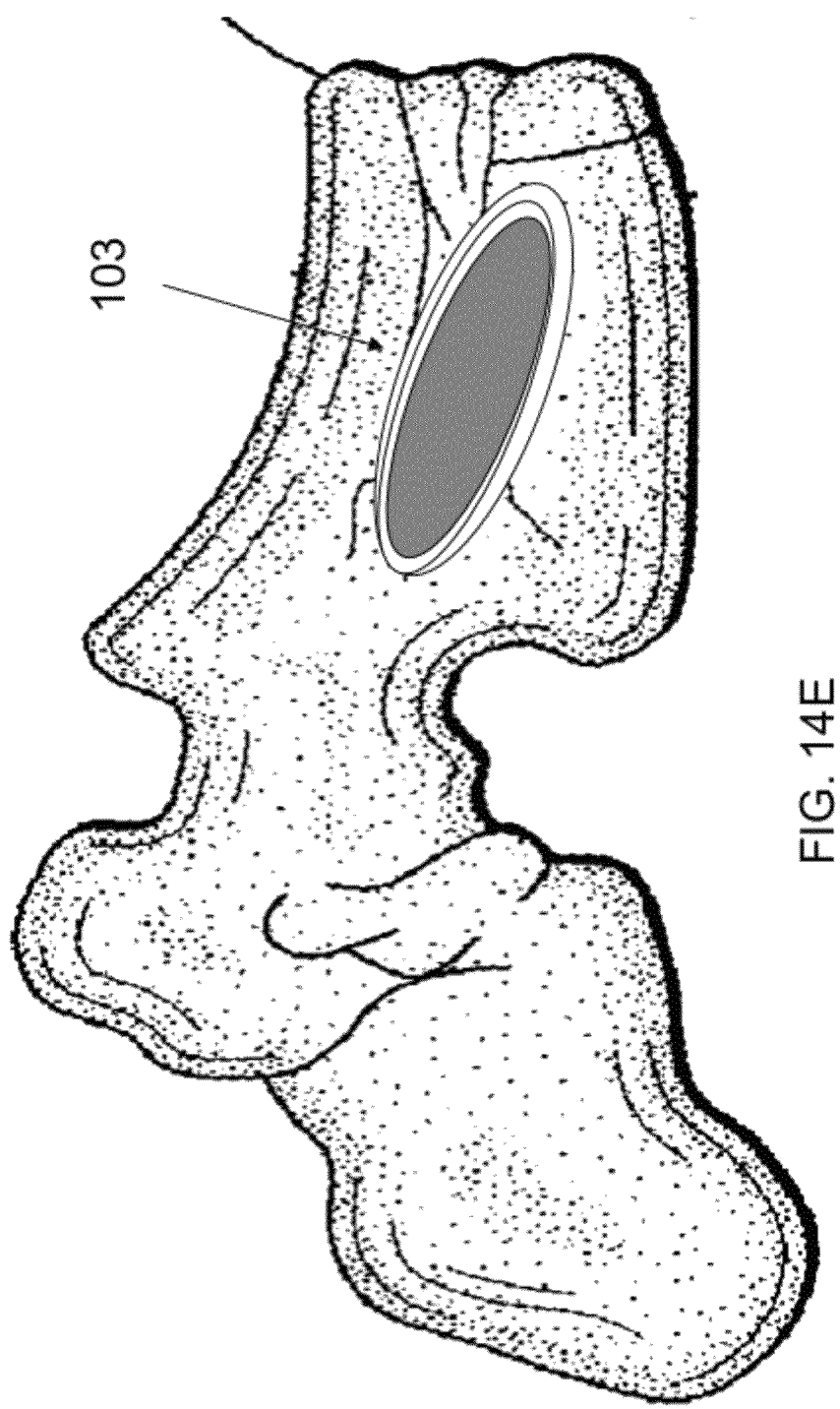

Once the light-sensitive fluid 707 inside the inmost inner cavity 223 is cured, the outer balloon 201 may be deflated by withdrawing the inflation fluid 705 from the outmost inner cavity 219, as shown in FIG. 14D, although the step of removing the inflation fluid 705 from the outmost inner cavity 219 is optional. If desired, the above process may be repeated for the intermediate inner balloon 205 to adjust the height of the collapsed or fractured vertebra 703. In an embodiment, the intermediate inner balloon 205 may be moved from a deflated state to an inflated state after the outer balloon 201 is deflated to fill in space inside the collapsed or fractured vertebra 703 vacated by the outer balloon 201. This enables the user to precisely adjust the collapsed or fractured vertebra 703 to the desired height. Moreover, if desired, the outmost inner cavity 219 may also be filled with the light sensitive liquid, which may be cured from inside out using the optical fiber 106 in the outmost inner cavity. Finally, once the expandable member 103 is set, it can be separated from the balloon catheter 110, so the balloon catheter 110 can be removed, as shown in FIG. 14E.

Figure 15A:
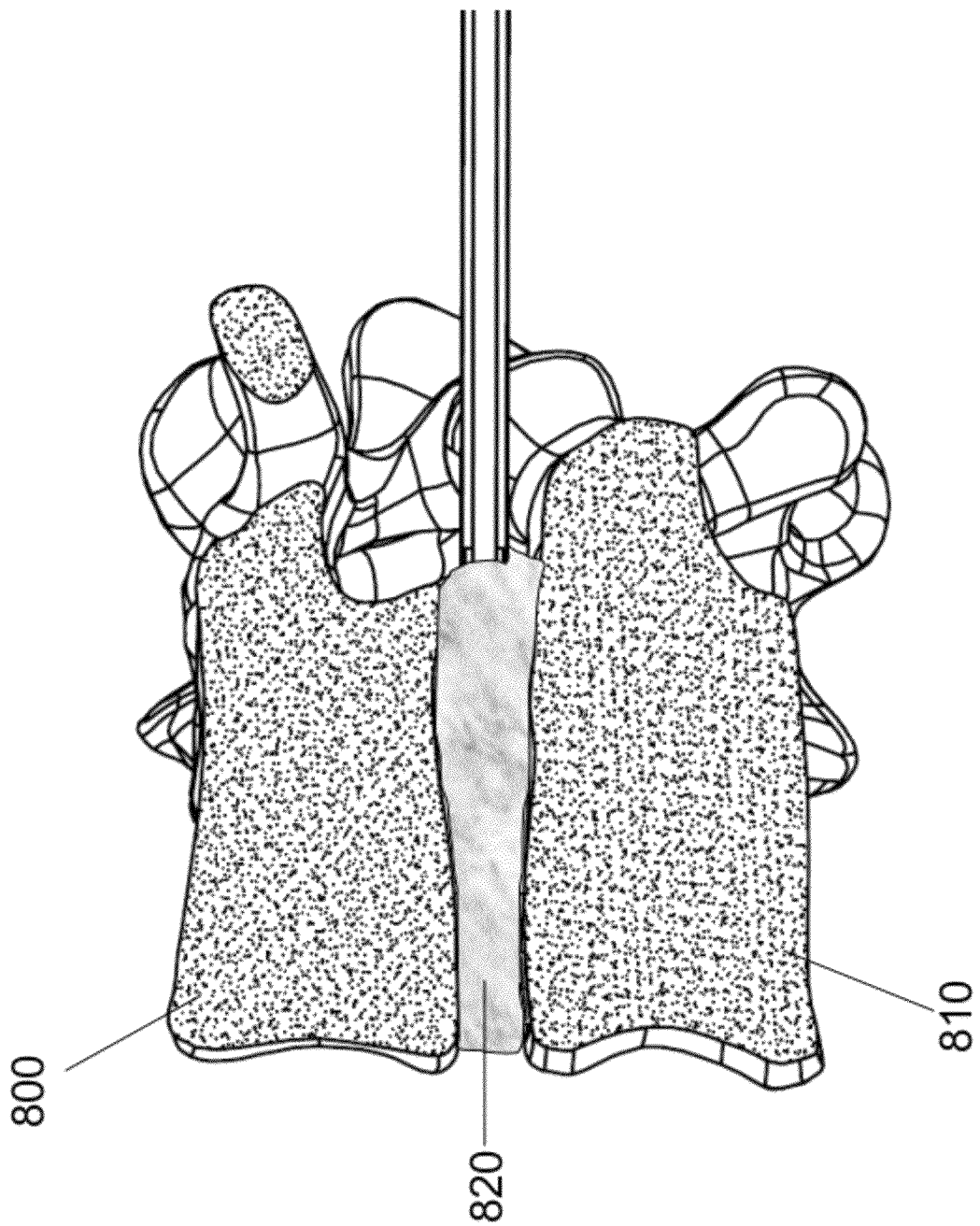
FIGS. 15A-15E show an embodiment of method steps for replacing a degenerative disc using components of the present disclosure.
Figure 15B:
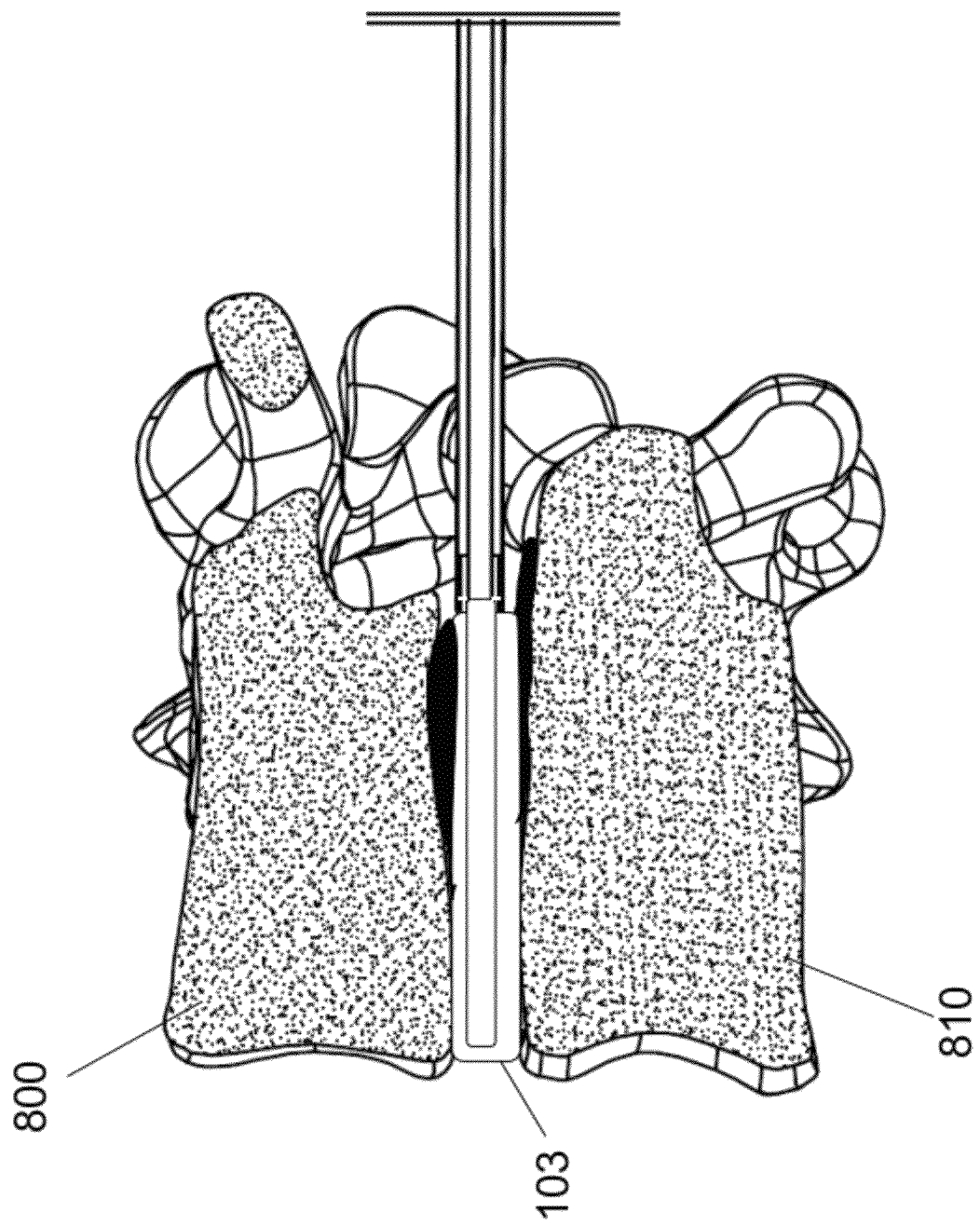
Figure 15C:
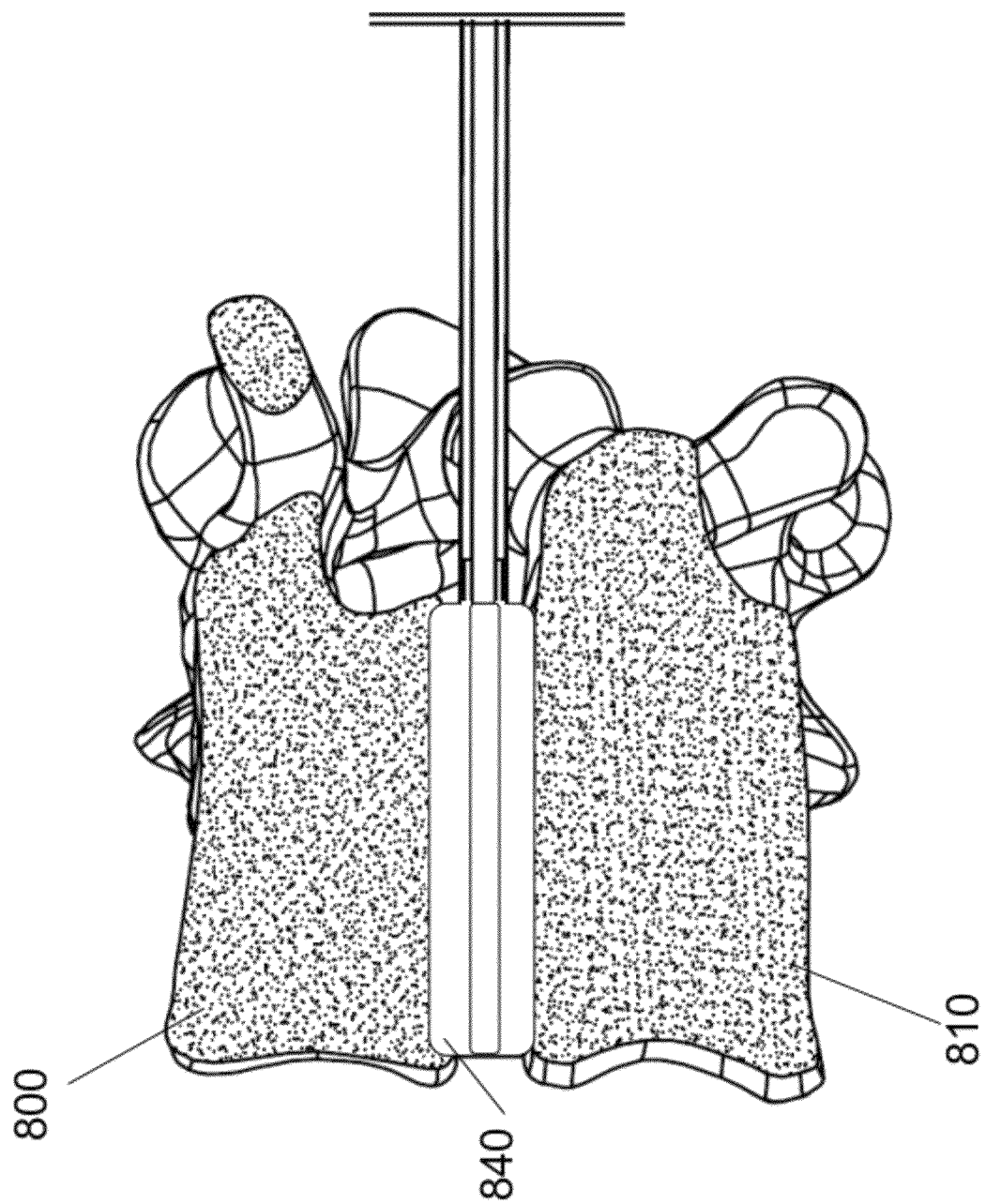
Figure 15D:
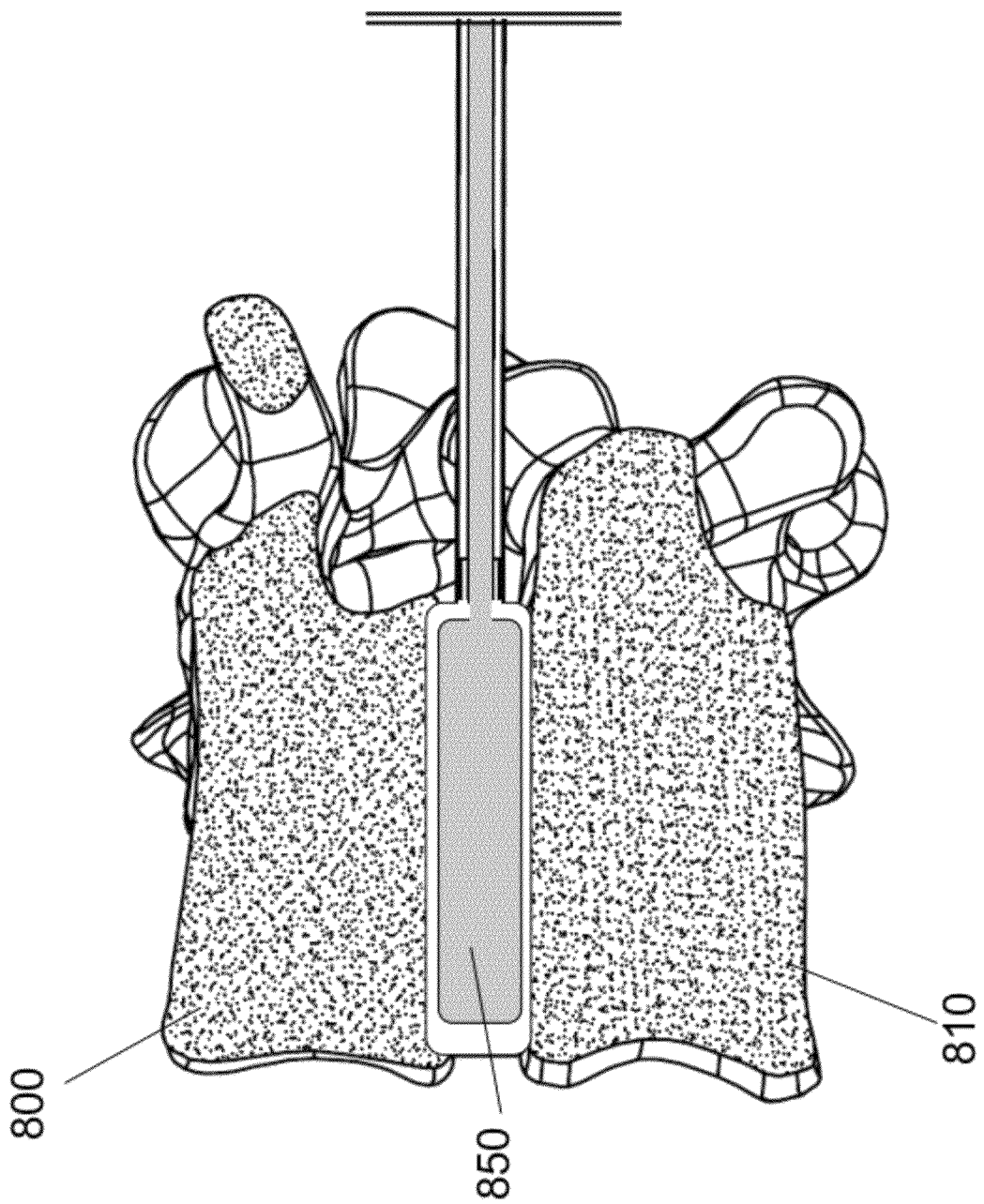
Figure 15E:
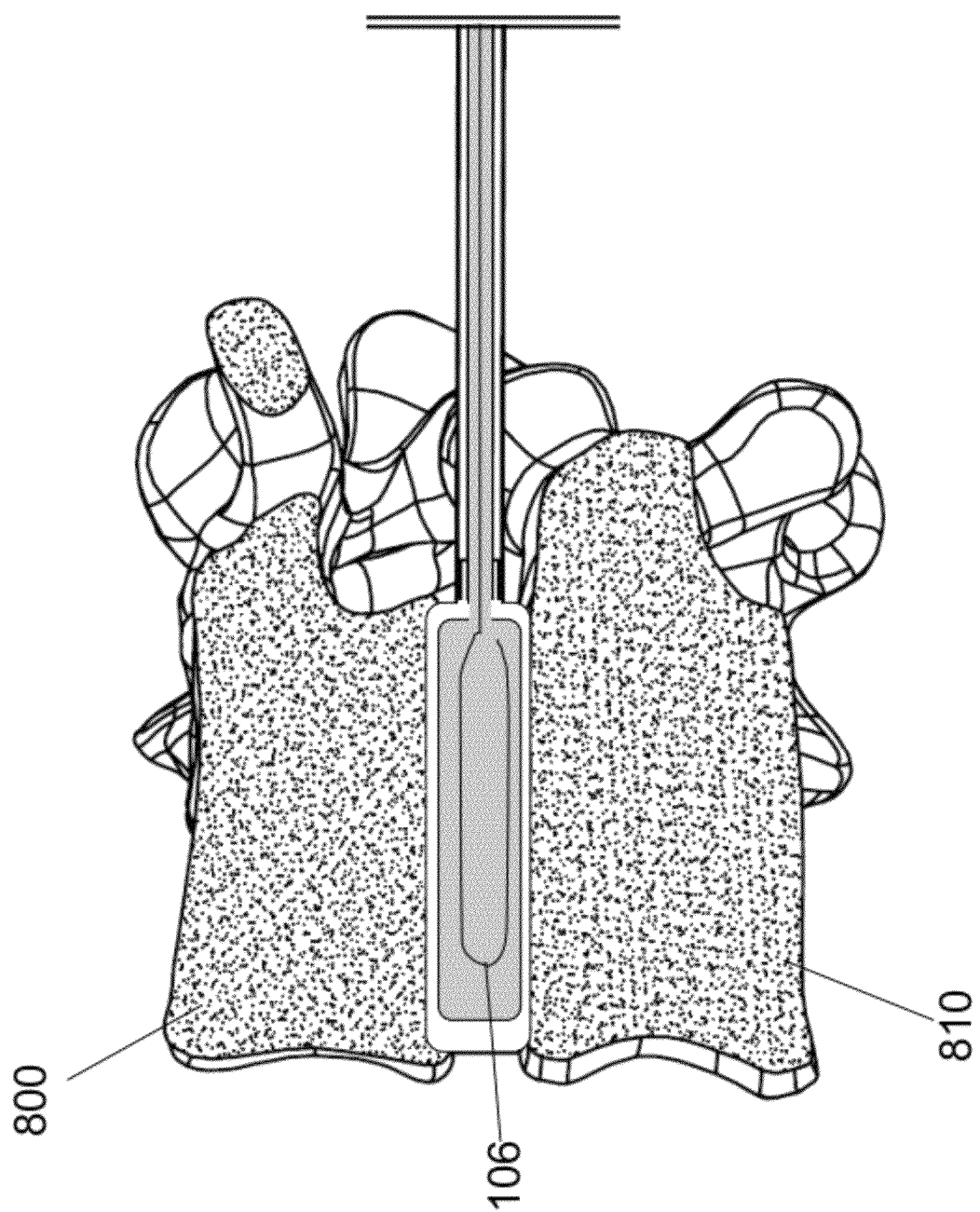

A device of the present disclosure may be used to replace an intervertebral disc. FIGS. 15A-15E illustrate an embodiment of the method steps for replacing a degenerative disc 820 positioned between two vertebrae 800, 810, using components of the present disclosure. The method includes removing the degenerative disc 820 to create a space, as illustrated in FIG. 15A, and delivering, in an unexpanded state, an expandable member 103 having at least a first inner balloon positioned inside and completely surrounded by an outer balloon to the space, as illustrated in FIG. 15B. Once the expandable member 103 is properly positioned, an inflation fluid 840 is injected into the outer balloon to expand the outer balloon and to temporarily restore native disc height, as illustrated in FIG. 15C. While maintaining the expanded outer balloon, a light-curable fluid 850 is injected into the inner balloon to expand the inner balloon within the expanded outer balloon, as illustrated in FIG. 15D. An optical fiber 106 of the present disclosure, having any of the nonlinear light-emitting portions described herein and sufficiently designed to emit light energy along a length of the optical fiber, is positioned inside the expandable member 103, as illustrated in FIG. 15E. The optical fiber 106 is connected to a light source (not visible) which is activated to cure the light-curable fluid 850 inside the inner balloon to harden the inner balloon within the expanded outer balloon. The inflation fluid 840 that was injected into the outer balloon can either remain inside the outer balloon, or can be removed from the outer balloon. The optical fiber 106 that was positioned within the expandable member 103 can either remain inside the expandable member 103, or can be removed from the expandable member 103. At the end of the procedure, the hardened expandable member 103 is removed from the balloon catheter and remains in position, thus replacing the degenerative disc 820.

A method for repairing a vertebral compression fracture includes positioning an expandable member releasably disposed at a distal end of a balloon catheter within a cancellous bone region of a fractured or collapsed vertebra, wherein the expandable member comprises an outer balloon and one or more inner balloons; moving the outer balloon from a deflated state to an inflated state to expand the collapsed or fractured vertebra to a desired height; moving one or more inner balloons from a deflated state to an inflated state with a light-sensitive fluid; introducing a pre-shaped optical fiber into an inner cavity within the outer balloon; activating the optical fiber to uniformly cure the light-sensitive fluid within the one or more inner balloons; moving the outer balloon from the inflated state to the deflated state; and releasing the expandable member from the balloon catheter.

A method for replacing a degenerative disc includes removing a degenerative disc to create a space; delivering, in an unexpanded state, an expandable member having a first inner balloon positioned inside and completely surrounded by an outer balloon to the space; injecting an inflation fluid into the outer balloon to expand the outer balloon and to temporarily restore native disc height; maintaining the expanded outer balloon while injecting a light-curable fluid into the inner balloon to expand the inner balloon within the expanded outer balloon; positioning an optical fiber sufficiently designed to emit light energy along a length of the optical fiber inside the expandable member, wherein the optical fiber is connected to a light source; activating the light source; delivering light energy to the optical fiber from the light source; and curing the light-curable fluid inside the inner balloon to harden the inner balloon within the expanded outer balloon.

A method for repairing a vertebral compression fracture includes gaining access to a fractured area of a collapsed vertebrae; providing a balloon catheter having an elongated shaft with a proximal end, a distal end, and a longitudinal axis therebetween, the balloon catheter comprising: at least one inner lumen incorporated within the elongated shaft; an expandable member including an inner inflatable balloon positioned inside and completely surrounded by an outer inflatable balloon, the expandable member located at the distal end; and a multipurpose adapter for passage of at least one of an inflation fluid or a medical instrument, the multipurpose adapter located at the proximal end; positioning the expandable member, in a deflated state, in the fractured area of the collapsed vertebrae; injecting a first inflation fluid into the outer inflatable balloon of the expandable member to inflate the outer inflatable balloon and temporarily restore height of the collapsed vertebrae; injecting a second light-curable inflation fluid into the inner inflatable balloon of the expandable member to inflate the inner inflatable balloon; providing a flexible optical fiber having a core surrounded by a cladding material, the optical fiber comprising an outer diameter sized to pass through the inner lumen of the elongated shaft of the balloon catheter; a nonlinear light-emitting portion of a given length, wherein a portion of the cladding material from the nonlinear light-emitting portion has been removed so that light energy may be dispersed along the length of the nonlinear light-emitting portion; and a linear elongated portion for guiding light towards the nonlinear light-emitting portion; advancing the nonlinear light-emitting portion of the optical fiber through the inner lumen of the elongated shaft of the balloon catheter in a stretched condition in which the nonlinear light-emitting portion of the optical fiber has a linear conformation, and releasing the nonlinear light-emitting portion of the optical fiber into the expandable member in a relaxed condition in which the nonlinear light-emitting portion of the optical fiber assumes a curved conformation; activating a light source that is connected to the optical fiber so the nonlinear light-emitting portion of the optical fiber disperses light energy at a terminating face and along a length of the optical fiber to communicate light energy to cure the second light-curable inflation fluid; and releasing the hardened expandable member from the balloon catheter.

A device includes a balloon catheter having an elongated shaft with a proximal end, a distal end, and a longitudinal axis therebetween, the balloon catheter comprising at least one inner lumen incorporated within the elongated shaft; an inner balloon positioned inside and completely surrounded by an outer balloon, the balloons located at the distal end; and an adapter for passage of at least one of an inflation fluid or a medical instrument, the adapter located at the proximal end; and an optical fiber having a core surrounded by a cladding material, the optical fiber comprising an outer diameter sized to pass through the inner lumen of the elongated shaft of the balloon catheter; a nonlinear light-emitting portion of a given length, wherein a portion of the cladding material from the nonlinear light-emitting portion has been removed so that light energy may be emitted along the length of the nonlinear light-emitting portion; and a linear elongated portion for guiding light towards the nonlinear light-emitting portion.

A device includes a balloon catheter having an elongated shaft with a proximal end, a distal end, and a longitudinal axis therebetween; an expandable member releasably disposed at a distal end of the balloon catheter, the expandable member comprising an outer balloon and one or more inner balloons; and an optical fiber having a pre-shaped distal portion, wherein the balloon catheter includes a plurality of inner lumens in fluid communication with a plurality of inner cavities within the expandable member for passing the optical fiber, an inflation fluid, and a light-sensitive fluid to the plurality of inner cavities within the expandable member, and wherein the optical fiber is configured to emit light along at least a part of the pre-shaped distal portion of the optical fiber.

A system includes a balloon catheter having an elongated shaft with a proximal end, a distal end, and a longitudinal axis therebetween, the balloon catheter comprising at least one inner lumen incorporated within the elongated shaft; at least a first inner inflatable balloon positioned inside and completely surrounded by an outer inflatable balloon, the balloons located at the distal end; and an adapter for passage of at least one of an inflation fluid or a medical instrument, the adapter located at the proximal end; an optical fiber having a core surrounded by a cladding material, the optical fiber comprising an outer diameter sized to pass through the inner lumen of the elongated shaft of the balloon catheter; a nonlinear light-emitting portion of a given length, wherein a portion of the cladding material from the nonlinear light-emitting portion has been removed so that light energy may be emitted along the length of the nonlinear light-emitting portion; a linear elongated portion for guiding light towards the nonlinear light-emitting portion; a relaxed condition in which the nonlinear light-emitting portion of the optical fiber assumes a curved conformation; a stretched condition in which the nonlinear light-emitting portion of the optical fiber has a linear conformation in which the nonlinear light-emitting portion of the optical fiber can be advanced through the inner lumen of the elongated shaft of the balloon catheter; and a memory which returns the nonlinear light-emitting portion from the stretched condition to the relaxed condition; a light-sensitive fluid; and a light source.

All patents, patent applications, and published references cited herein are hereby incorporated by reference in their entirety. It will be appreciated that several of the above-disclosed and other features and functions, or alternatives thereof, may be desirably combined into many other different systems or applications.

What is claimed is:

1. A device comprising:
   a balloon catheter having an elongated shaft with a proximal end, a distal end, and a longitudinal axis therebetween, the balloon catheter comprising:
   at least one inner lumen incorporated within the elongated shaft;
   two or more inflatable balloons including at least a first inner inflatable balloon positioned inside and completely surrounded by a first outer inflatable balloon, the balloons located at the distal end; and
   an adapter for passage of at least one of an inflation fluid or a medical instrument, the adapter located at the proximal end; and
   an optical fiber having a core surrounded by a cladding material, the optical fiber comprising:
   an outer diameter sized to pass through the inner lumen of the elongated shaft of the balloon catheter and into one of the two or more inflatable balloons to cure the inflation fluid in at least one inflatable balloon of the two or more inflatable balloons;
   a nonlinear light-emitting portion of a given length, the nonlinear light-emitting portion including a plurality of spaced apart cuts in the cladding material along a length of the nonlinear light-emitting portion exposing the core so that light energy may be emitted from the core along the length of the nonlinear light-emitting portion; and
   a linear elongated portion for guiding light towards the nonlinear light-emitting portion,
   wherein the optical fiber has a curved conformation in which the nonlinear light-emitting portion of the optical fiber forms at least one loop around the first inner inflatable balloon from inside the first outer inflatable balloon, and
   wherein spaces between the cuts decrease toward a distal end of the optical fiber to harden the light-sensitive fluid in a substantially circumferential uniform light intensity when the optical fiber is in the curved conformation.

2. The device of claim 1 wherein the balloon catheter has an outside diameter ranging from about 3 mm to about 8 mm.

3. The device of claim 1 wherein the optical fiber has an outside diameter ranging from about 0.75 mm to about 2.0 mm.

4. The device of claim 1 wherein the first inner inflatable balloon and the first outer inflatable balloon are concentric relative to one another.

5. The device of claim 1 wherein the optical fiber further comprises:
   a relaxed condition in which the nonlinear light-emitting portion of the optical fiber assumes the curved conformation;
   a stretched condition in which the nonlinear light-emitting portion of the optical fiber has a linear conformation in which the nonlinear light-emitting portion of the optical fiber can be advanced through the inner lumen of the elongated shaft of the balloon catheter; and
   a memory which returns the nonlinear light-emitting portion from the stretched condition to the relaxed condition.

6. The device of claim 5 wherein the curved conformation of the nonlinear light-emitting portion forms a candy cane shape.

7. The device of claim 5 wherein the curved conformation of the nonlinear light-emitting portion forms a U shape.

8. The device of claim 5 wherein the curved conformation of the nonlinear light-emitting portion forms a coiled shape having multiple loops.

9. The device of claim 5 wherein the curved conformation of the nonlinear light-emitting portion forms a convoluted shape.

10. The device of claim 5 wherein the nonlinear light-emitting portion includes cuts in the cladding material forming a helical design along a length of the optical fiber.

11. The device of claim 1 wherein the two inflatable balloons have a diameter size ranging from about 0.5 mm to about 50 mm.

12. The device of claim 1 wherein the optical fiber includes a bend radius of approximately 6 times a diameter of the optical fiber, a temperature stability of up to approximately 90° C., an acceptance angle of approximately 80° and a refractive index core of approximately 1.48 or greater.

13. The device of claim 1 wherein each cut in the cladding material causes an internal reflectance from the core to be directed outwards at an angle, wherein each angle changes along the length of the nonlinear light-emitting portion relative to an amount of light dispersed.

14. The device of claim 1 wherein each cut in the cladding material causes an internal reflectance from the core to be directed outwards at an angle, wherein cuts located approximate a distal end and a proximal end of the balloon include a shallower angle than cuts positioned at a middle of the balloon.

15. The device of claim 1 wherein the optical fiber curves around at least one inflatable balloon of the two or more inflatable balloons by one of: (a) curving around an outer wall or an inner wall of the at least one inflatable balloon of the two or more inflatable balloons; (b) curving around an outer wall of the first inner inflatable balloon in a separate optical fiber conduit; and (c) curving inside an inner wall of the first inner inflatable balloon in a separate optical fiber conduit.

16. The device of claim 1 wherein optical fiber uniformly disperses light radially from one of (a) an outside of the first inner inflatable balloon towards an inside of the first inner inflatable balloon to cure the light-sensitive fluid contained therein or (b) an inside the first inner inflatable balloon toward an outside of the first inner inflatable balloon to cure the light-sensitive fluid contained therein.

17. A system comprising:
   a balloon catheter having an elongated shaft with a proximal end, a distal end, and a longitudinal axis therebetween, the balloon catheter comprising:
   at least one inner lumen incorporated within the elongated shaft;
   two or more inflatable balloons including at least a first inner inflatable balloon positioned inside and completely surrounded by a first outer inflatable balloon, the balloons located at the distal end; and
   a multipurpose adapter for passage of at least one of an inflation fluid or a medical instrument, the multipurpose adapter located at the proximal end;

an optical fiber having a core surrounded by a cladding material, the optical fiber comprising:

an outer diameter sized to pass through the inner lumen of the elongated shaft of the balloon catheter and into one of the two or more inflatable balloons to cure the inflation fluid in at least one inflatable balloon of the two or more inflatable balloons;

a nonlinear light-emitting portion of a given length, the nonlinear light-emitting portion including a plurality of spaced apart cuts in the cladding material along a length of the nonlinear light-emitting portion exposing the core so that light energy may be emitted from the core along the length of the nonlinear light-emitting portion;

a linear elongated portion for guiding light towards the nonlinear light-emitting portion;

a relaxed condition in which the nonlinear light-emitting portion of the optical fiber assumes a curved conformation, in which the nonlinear light-emitting portion of the optical fiber forming at least one loop around the first inner inflatable balloon from inside the first outer inflatable balloon, wherein spaces between the cuts decrease toward a distal end of the optical fiber to harden the light-sensitive fluid in a substantially circumferential uniform light intensity when the optical fiber is in the curved conformation;

a stretched condition in which the nonlinear light-emitting portion of the optical fiber has a linear conformation in which the nonlinear light-emitting portion of the optical fiber can be advanced through the inner lumen of the elongated shaft of the balloon catheter; and a memory which returns the nonlinear light-emitting portion from the stretched condition to the relaxed condition;

a light-sensitive fluid; and a light source.

18. The system of claim 17 wherein the first inner inflatable balloon and the first outer inflatable balloon are concentric relative to one another.

19. The system of claim 17 wherein the curved conformation of the nonlinear light-emitting portion forms one of a candy cane shape, a U shape or a coiled shape having multiple loops.

20. The system of claim 17 wherein the curved conformation of the nonlinear light-emitting portion forms a convoluted shape.

21. The system of claim 17 wherein the light-sensitive fluid has a viscosity ranging from about 650 cP to about 450 cP.

22. The system of claim 17 wherein the nonlinear light-emitting portion includes cuts in the cladding material forming a helical design along a length of the optical fiber.

23. A device comprising:

a catheter having an elongated shaft with a proximal end, a distal end, and a longitudinal axis therebetween, at least one inner lumen incorporated within the elongated shaft;

two expandable members located at the distal end of the catheter and being in communication with the at least one inner lumen, the two expandable members comprising an outer expandable balloon and an inner expandable balloon;

an adapter located at the proximal end of the catheter for passage of at least one of an inflation fluid or a medical instrument into the expandable member through the catheter; and an optical fiber having a core surrounded by a cladding material, the optical fiber comprising:

an outer diameter sized to pass through the at least one inner lumen of the catheter and into one of the two expandable members to cure the inflation fluid in at least one expandable member of the two expandable members;

a nonlinear light-emitting portion having a length, the nonlinear light-emitting portion including a plurality of spaced apart cuts in the cladding material along a length of the nonlinear light-emitting portion exposing the core so that light energy may be emitted from the core along the length of the nonlinear light-emitting portion; and a linear elongated portion for guiding light towards the nonlinear light-emitting portion, wherein the optical fiber has a curved conformation in which the nonlinear light-emitting portion of the optical fiber forms at least one loop around the first inner inflatable balloon from inside the first outer inflatable balloon, and wherein spaces between the cuts decrease toward a distal end of the optical fiber to harden the light-sensitive fluid in a substantially circumferential uniform light intensity when the optical fiber is in the curved conformation.

24. The device of claim 23 wherein the optical fiber further comprises:

a relaxed condition in which the nonlinear light-emitting portion of the optical fiber assumes a curved shape;

a stretched condition in which the nonlinear light-emitting portion of the optical fiber has a linear shape in which the nonlinear light-emitting portion of the optical fiber can be advanced through the inner lumen of the elongated shaft of the balloon catheter; and a memory which returns the nonlinear light-emitting portion from the stretched condition to the relaxed condition.

* * * * *